(12) United States Patent
Chen

(10) Patent No.: US 11,389,085 B2
(45) Date of Patent: Jul. 19, 2022

(54) HUMAN PHYSICAL FUNCTIONAL ABILITY AND MUSCLE ABILITY COMPREHENSIVE ASSESSMENT SYSTEM AND METHOD THEREOF

(71) Applicant: Yan Chen, Shanghai (CN)

(72) Inventor: Yan Chen, Shanghai (CN)

( * ) Notice: Subject to any disclaimer, the term of this patent is extended or adjusted under 35 U.S.C. 154(b) by 559 days.

(21) Appl. No.: 16/201,893

(22) Filed: Nov. 27, 2018

(65) Prior Publication Data
US 2019/0175078 A1 Jun. 13, 2019

(30) Foreign Application Priority Data

Jun. 5, 2018 (CN) .......................... 201810582779.0

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/1036* (2013.01); *A61B 5/1121* (2013.01);
(Continued)

(58) Field of Classification Search
CPC ........ A61B 2505/09; A61B 2562/0219; A61B 5/1036; A61B 5/1121; A61B 5/1128;
(Continued)

(56) References Cited

U.S. PATENT DOCUMENTS

| 9,283,429 | B2 * | 3/2016 | Aragones | A63B 24/00 |
| 9,526,946 | B1 * | 12/2016 | Zets | A61B 5/6892 |
| 9,773,330 | B1 * | 9/2017 | Douglas | G06F 3/0346 |
| 2001/0052005 | A1 * | 12/2001 | Lachaud | G06F 9/54 709/221 |

(Continued)

FOREIGN PATENT DOCUMENTS

WO WO-2017045027 A1 * 3/2017 ............. G16H 10/60

OTHER PUBLICATIONS

Anne Schmitz, et al. "The measurement of in vivo joint angles during a squat using a single camera markerless motion capture system as compared to a marker based system, Gait & Posture." vol. 41, Issue 2, 2015, pp. 694-698, ISSN 0966-6362, https://doi.org/10.1016/j.gaitpost.2015.01.028. (Year: 2015).*

(Continued)

*Primary Examiner* — Sean P Dougherty
*Assistant Examiner* — Alexander H Connor

(57) ABSTRACT

A human physical functional ability and muscle ability comprehensive assessment system includes: a force measuring system, for measuring physical quantities related to used forces of a participant during a process of completing a fitness movement by the participant; a motion capture system, for measuring physical quantities related to body posture changes of the participant during the process of completing the fitness movement; a signal collecting system, for collecting the physical quantities related to the used forces sent from the force measuring system and collecting the physical quantities related to the physical posture changes (Continued)

sent from the motion capture system, and for processing original data of the physical quantities with time synchronization; and an information processing system, for calculating the data after time synchronization and obtaining multiple characteristic parameters which represent muscle characteristics and/or joint characteristics. Thereof, a muscle quality and a joint quality of the participant can be judged.

4 Claims, 16 Drawing Sheets

(51) Int. Cl.
    *A61B 5/103*     (2006.01)
    *A61B 5/22*     (2006.01)
    *G16H 20/30*     (2018.01)
    *G06V 40/20*     (2022.01)

(52) U.S. Cl.
    CPC .......... *A61B 5/6802* (2013.01); *A61B 5/6892* (2013.01); *A61B 5/7275* (2013.01); *A61B 5/224* (2013.01); *A61B 2505/09* (2013.01); *A61B 2562/0219* (2013.01); *G06V 40/23* (2022.01); *G16H 20/30* (2018.01)

(58) Field of Classification Search
    CPC ..... A61B 5/224; A61B 5/6802; A61B 5/6892; A61B 5/7275; G06K 9/00342; G16H 20/30; G16H 40/63; G16H 50/30
    See application file for complete search history.

(56) References Cited

U.S. PATENT DOCUMENTS

| | | | | |
|---|---|---|---|---|
| 2013/0338802 | A1* | 12/2013 | Winsper | A63B 24/0075 700/92 |
| 2016/0144236 | A1* | 5/2016 | Ko | G16H 20/30 434/247 |
| 2017/0368413 | A1* | 12/2017 | Shavit | G06K 9/00342 |

OTHER PUBLICATIONS

Scorza A, Massaroni C, Orsini F, et al. A Review on Methods and Devices for Force Platforms Calibration in Medical Applications. Journal of Engineering Science & Technology Review. 2018;11(1):10-18. doi:10.25103/jestr.111.02 (Year: 2018).*

Hussein Lopez-Nava I, Munoz-Melendez A. Wearable Inertial Sensors for Human Motion Analysis: A Review. IEEE sensors journal. 2016;(22):7821. Accessed Jun. 7, 2021. http://search.ebscohost.com/login.aspx?direct=true&db=edsbl&AN=vdc.100086126769.0x000001&site=eds-live&scope=site (Year: 2016).*

Lin JFS, Kulić D. Human pose recovery using wireless inertial measurement units. Physiological measurement. 2012;33(12):2099-2115. doi:10.1088/0967-3334/33/12/2099 (Year: 2012).*

\* cited by examiner

HUMAN PHYSICAL FUNCTIONAL ABILITY AND MUSCLE ABILITY COMPREHENSIVE ASSESSMENT SYSTEM AND METHOD THEREOF

CROSS REFERENCE OF RELATED APPLICATION

The application claims priority under 35 U.S.C. 119(a-d) to CN 201810582779.0, filed Jun. 5, 2018.

BACKGROUND OF THE PRESENT INVENTION

Field of Invention

The present invention relates to a technical field of physical sports ability test, and more particularly to a human physical functional ability and muscle ability comprehensive assessment system and a method thereof.

Description of Related Arts

For the high-level fitness, professional sports training and health medical rehabilitation, we need to know the comprehensive characteristics of one muscle or one muscle group of one person, including the muscle strength, the muscle endurance, and the muscle explosiveness. However, the conventional physical sports ability assessment methods have problems as follows.

Firstly, in the common methods, merely one muscle characteristic is generally tested; for example, most of the methods merely test the muscle strength. Secondly, many methods adopt the manual visual inspection with the subjective judgment, or utilize the simple measuring means (for example, measuring the jumping and leg ability through vertical jumping and reaching, and assessing the upper body strength with the number of push-ups). The above measuring methods have the limitations that the measured data is too singular. For example, the strength and the explosiveness of each muscle involved in jumping cannot be obtained through the jumping height, which are important to the follow-up targeted training; and the number of push-ups cannot reflect the upper body strength, the muscle endurance and the fatigue points of one person. Thirdly, some conventional force measuring devices provide the single function. For example, while some of the force measuring devices can complete the measurement of the parameters such as the leg strength through measurement of vertical jumping, the devices lack assistance of the motion capture equipment, so that the analysis of body and joint movement cannot be completed merely with the measured parameters such as the leg strength. Fourthly, although some wearable devices or image analysis software can analyze the human motion process, they are unable to form the important analysis of muscle strength, joint angles and forces due to lacking the assistance of the accurate force measuring device. Fifthly, some methods require the relatively cumbersome process to generate the characteristic analysis of muscles of the whole body, which has relatively high requirements on time, space and labor cost.

The Chinese patent application CN 201710267805.6 disclosed a sports biomechanics coupling analysis system, comprising a test device, a wireless synchronous trigger device and a human-machine interaction software system, wherein: the test device comprises a variable-speed force measuring treadmill, an insole-type plantar measuring device, an optical motion capture device, a high-speed photographing device and a wireless myoelectric measuring device; the wireless synchronous trigger device controls the test device through emitting a synchronous pulse, which realizes the signal synchronous collection and storage of biokinetic and kinetic parameters; the human-machine interaction software system comprises a biomechanical model testing module, a parameter setting module, a data batch processing module, a preprocessing module of optically capturing the test data, a data analyzing module, and a database storing and manual playback analyzing module, which is able to realize the in-vivo real-time accurate coupling quantitative analysis of kinetic parameters, motion mechanism and motion rule of the biological motion. The above technical solution is merely for obtaining the mechanical property parameters of the biological motion, but does not disclose how to make the physical assessment of the creatures in motion according to the measured parameters.

SUMMARY OF THE PRESENT INVENTION

An object of the present invention is to provide a human physical functional ability and muscle ability comprehensive assessment system, so as to solve the problem that conventional physical sports ability measuring devices provide single species of data and single function.

In order to accomplish the above object, the present invention provides a human physical functional ability and muscle ability comprehensive assessment system, comprising:

a force measuring system, for measuring physical quantities related to used forces of a participant during a process of completing a fitness movement by the participant;

a motion capture system, for measuring physical quantities related to body posture changes of the participant during the process of completing the fitness movement by the participant;

a signal collecting system, for collecting the physical quantities related to the used forces which are sent from the force measuring system and collecting the physical quantities related to the physical posture changes which are sent from the motion capture system, and for processing original data of the physical quantities with time synchronization; and an information processing system, for calculating the data after time synchronization and obtaining multiple characteristic parameters which represent muscle characteristics and/or joint characteristics.

Preferably, the information processing system comprises:

a calculating unit, for calculating the data after time synchronization and obtaining the multiple characteristic parameters which represent the muscle characteristics and/or the joint characteristics;

a classifying unit, for, according to categories of the muscle characteristics and/or the joint characteristics, classifying the characteristic parameters into parameter sets of the corresponding categories; and a score-generating unit, for individually scoring the different characteristic parameters in each parameter set, obtaining an individual score of each characteristic parameter, then weighting according to a relevancy to the corresponding category of the muscle characteristics and/or the joint characteristics, and obtaining a parameter composite score of a specified muscle group and/or joint corresponding to the fitness movement.

Preferably, the force measuring system adopts two pressure mats sharing the same structure; the pressure mats are rectangular; four weighing sensors are respectively arranged at four corners of each pressure mat; a pressure signal processing board is arranged at a center of each pressure mat; a metal cover plate is arranged on the weighing sensors and the pressure signal processing board of each pressure mat and is supported by the four weighing sensors; an output end of each weighing sensor is connected with the pressure signal processing board; an output end of the pressure signal processing board is connected to the signal collecting system, for sending a pressure of the participant on each pressure mat and data about a gravity center position on each pressure mat to the signal collecting system.

Preferably, the motion capture system adopts at least two inertial sensors; each inertial sensor is formed by at least one of an accelerometer, a gyroscope and a magnetometer, which are respectively for measuring data about an acceleration, an angular velocity and a geomagnetic field; each inertial sensor further comprises an antenna; the inertial sensors are fixed on the participant, for wirelessly transmitting body posture data of the participant to the signal collecting system.

Preferably, the signal collecting system comprises multiple input interfaces, multiple wireless signal receiving devices, and a central data collecting and processing unit, wherein: the input interfaces are connected with the force measuring system; the wireless signal receiving devices communicate with the motion capture system; the central data collecting and processing unit adopts an FPGA (field programmable gate array) chip for processing the collected data with time synchronization.

Preferably, the information processing system adopts a computer and is connected with a display device and an input device.

Preferably, the force measuring system adopts a muscle strength measuring device, for measuring and outputting an absolute value of a muscle contraction force of a muscle group related to the fitness movement.

Preferably, the motion capture system adopts at least one photographing system and more than one visual identification tag; the visual identification tags are fixed on the participant; the photographing system captures motion image data about body postures related to movement of targeted body parts of the participant; and, a movement speed, a movement direction and a rotational speed of each visual identification tag are extracted, so as to obtain the body posture data of the participant.

The present invention also provides a human physical functional ability and muscle ability comprehensive assessment method, comprising steps of:

(S1), measuring physical quantities related to used forces and/or physical quantities related to body posture changes of a participant during a process of completing a fitness movement by the participant;

(S2), collecting the measured physical quantities and processing with time synchronization;

(S3), calculating data after time synchronization, and obtaining multiple characteristic parameters which represent muscle characteristics and/or joint characteristics;

(S4), according to categories of the muscle characteristics and/or the joint characteristics, classifying the characteristic parameters into parameter sets of the corresponding categories; and (S5), individually scoring the different characteristic parameters in each parameter set, obtaining an individual score of each characteristic parameter, then weighting according to a relevancy to the corresponding category of the muscle characteristic and/or the joint characteristic, and obtaining a parameter composite score of a specified muscle group and/or joint corresponding to the fitness movement; wherein the fitness movement has at least one kind.

Preferably, in the step (S5), the step of "individually scoring the different characteristic parameters in each parameter set" particularly comprises steps of: dividing a large amount of the statistical characteristic parameters into multiple regions from large to small, wherein each region corresponds to one score, so that a standard score planning table is formed; comparing each measured characteristic parameter with the standard score planning table; and obtaining a corresponding individual score.

Preferably, after the step (S5), the method further comprises a step of:

(S6), comparing the parameter composite score of each parameter set with a standard parameter score, so as to grade the parameter composite score and obtain a level of each muscle characteristic and/or joint characteristic corresponding to the fitness movement.

Preferably, the standard parameter score is a set standard physical parameter value or a mean value of statistical data of the same age group.

Preferably, after the step (S5), the method further comprises a step of:

(S7), according to the parameter composite score or a level of each specified muscle group corresponding to the fitness movement, generating a series of muscle characteristic diagrams (such as a muscle strength diagram, a muscle explosiveness diagram, a muscle endurance diagram, and other diagrams display specific characteristics of muscles), wherein a position of each specified muscle group is marked in the muscle characteristic diagram and the muscle characteristics (such as muscle strength, explosiveness and endurance) are reflected through different colors; according to the parameter composite score or a level of each specified joint corresponding to the fitness movement, generating a series of joint characteristic diagrams (such as a joint range of motion diagram and a joint stability diagram), wherein a position of each specified joint is marked in the joint characteristic diagram and the joint characteristics (such as motion range and stability) are reflected through different colors.

Preferably, in the step (S1), the physical quantities related to the used forces of the participant are measured with a pressure mat, comprising a pressure of the participant on the pressure mat and a gravity center position on the pressure mat.

Preferably, in the step (S1), the physical quantities related to the body posture changes of the participant are measured with at least two inertial sensors, comprising an angular velocity and a linear acceleration; alternatively, the physical quantities related to the body posture changes of the participant are measured with at least one photographing device and more than one visual identification tag, comprising a movement speed and a rotational angular velocity.

Preferably, the fitness movement refers to at least one kind of push-up, vertical jumping, crunch, trunk forward bending, speed walking, one-leg standing and high-knee lift; the muscle characteristics comprise a muscle endurance, a muscle explosiveness and a muscle strength; the muscle strength comprises an upper body strength, a lower body strength and a core strength; through the movement of vertical jumping, characteristic parameters representing the muscle explosiveness and the lower body strength are able to be measured, comprising a thrust force, an explosiveness and a muscle balance degree of two legs; through the movement of push-up, characteristic parameters representing the upper body strength are able to be measured, comprising a total thrust force, an average thrust force, a maximum thrust force, fatigue points and a complete number; through the movement of crunch, characteristic parameters representing the core strength are able to be measured, comprising the complete number, the fatigue points and an average bending angle; and through the movement of high-knee lift, characteristic parameters representing the muscle endurance are able to be measured, comprising the complete number, a highest frequency, a time of reaching the highest frequency and a duration time at the highest frequency.

Preferably, through the multiple kinds of the fitness movements, parameter composite scores of other characteristics representing a physical sports ability are able to be measured; the other characteristics representing the physical sports ability comprise at least one of flexibility, balance degree and agility; through the movement of trunk forward bending, characteristic parameters representing the flexibility are able to be measured, comprising a forward bending angle and a time of reaching a maximum angle; through the movement of speed walking, characteristic parameters representing the agility are able to be measured, comprising the complete number, the highest frequency, the time of reaching the highest frequency and the duration time at the highest frequency; and through the movement of one-leg standing, characteristic parameters representing the balance degree are able to be measured, comprising a balance score, an average gravity center shift, an gravity center shift variance and a balance maintaining ratio.

Compared with the prior art, the technical solutions of the present invention have beneficial effects as follows.

Firstly, the present invention designs a human physical functional ability and muscle ability comprehensive assessment system, wherein: the physical quantities related to the used forces of the participant during the process of completing the fitness movement are measured through the force measuring system; the physical quantities related to the body posture changes of the participant during the process of completing the fitness movement are measured through the motion capture system; then the measured data of the physical quantities is collected through the signal collecting system and processed with time synchronization; through extraction and analysis of all of the data, multiple characteristic parameters able to represent the muscle characteristics and the joint characteristics of the human body are obtained and are directly outputted and displayed through the information processing system. Thereof, when the user requires knowing the quality ability of the specified muscle group or joint, through completing one fitness movement directly with the system, the muscle characteristics or joint characteristics of the user can be judged from the obtained characteristic parameter values.

Compared with the tradition manual measurement or simple measuring devices, the measuring time is shortened; the physical sports ability can be analyzed and assessed more quickly and more conveniently; through the automatic data collection and data processing, the obtained data is more scientific and more accurate.

Secondly, through completing different fitness movements with the system, the characteristic analysis about all involved muscle groups and joints in the fitness movements can be obtained, and a series of characteristic parameters of the whole body are generated. Compared with the traditional measuring devices that generally only the characteristics of a single body part corresponding to one fitness movement are able to be obtained, the system provided by the present invention can know the sports abilities of all the parts of the human body by one time, which greatly decreases the time and labor cost. Moreover, compared with some large measuring devices with a complete structure, the system provided by the present invention has a simple structure and can be assembled in a room or in a relatively small space, which decreases taken-up space and production cost.

Thirdly, the present invention further provides the human physical functional ability and muscle ability comprehensive assessment method based on the above system. With the method, the characteristic parameter value what the user wants to know can be quickly and directly obtained according to the calculation formula of each characteristic parameter; through individually scoring each characteristic parameter and then weighting the individual scores of all characteristic parameters of each muscle characteristic or joint characteristic according to the relevancy of each characteristic parameter to the related characteristic, the parameter composite score of each muscle characteristic or related characteristic is obtained; and through the parameter composite score, the strength of the corresponding muscle characteristic or joint characteristic is judged. Compared with the conventional methods that the strength is required to be judged with multiple characteristics, the present invention can assess the strength of the physical sports ability of one body part more directly and more simply with one parameter composite score, so that the user, the coach or the doctor can know the physical sports ability of the participant more quickly and more accurately.

Fourthly, the method compares the parameter composite score with the standard score, for obtaining the level value and quickly generating the muscle characteristic diagrams and the joint characteristic diagrams, so that the common participant who is not familiar with the biokinetics can directly know the own physical sports ability with the level value or the diagrams.

Fifthly, the method mainly designs seven fitness movements of vertical jumping, push-up, crunch, speed walking, trunk forward bending, one-leg standing and high-knee lift, which are able to generate the comprehensive characteristic analysis of the muscles and joints of each body part, such as the muscle endurance, muscle strength, muscle explosiveness, joint static motion range and joint dynamic flexibility. Moreover, the method is able to generate the characteristic diagrams which are able to reflect the physical abilities of the whole body, the upper body, the lower body or other local body parts, able to conveniently analyze the sports ability and potential of one person based on the system, and able to easily know the characteristic strength difference among the different muscle groups of one person, so as to give the advice of the suitable sporting event.

BRIEF DESCRIPTION OF THE DRAWINGS

In order to illustrate technical solutions in preferred embodiments of the present invention or in the prior art more clearly, the accompanying drawings referenced in the description of the preferred embodiments or the prior art are simply described as follows. Obviously, the described accompanying drawings are only some embodiments of the present invention; and persons of ordinary skill in the art can derive other drawings from the structures shown in the accompanying drawings without creative efforts.

In figures: 1: display device; 2: pressure mat; 3 and 4: image analysis systems; 5, 6 and 7: inertial sensors; 8, 9 and 10: wireless signal receiving devices; 11: central data collecting and processing unit; 12: signal collecting system; 13: information processing system; and 14: input device.

DETAILED DESCRIPTION OF THE PREFERRED EMBODIMENT

The technical solutions in the preferred embodiments of the present invention are clearly and completely described as follows with the accompanying drawings. Obviously, the described preferred embodiments are only a part of embodiments of the present invention, not all of the embodiments.

First Preferred Embodiment

Figure 1:
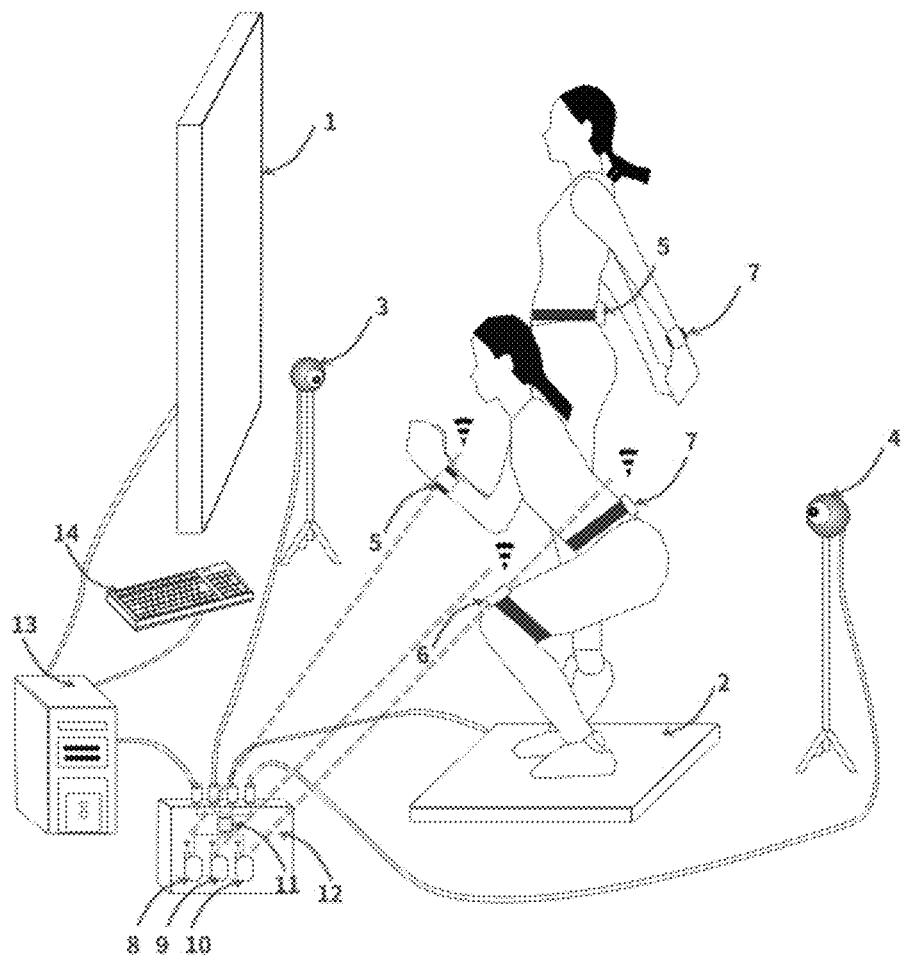
FIG. 1 is a first structural sketch view of a human physical functional ability and muscle ability comprehensive assessment system according to a first preferred embodiment of the present invention.
Figure 2:
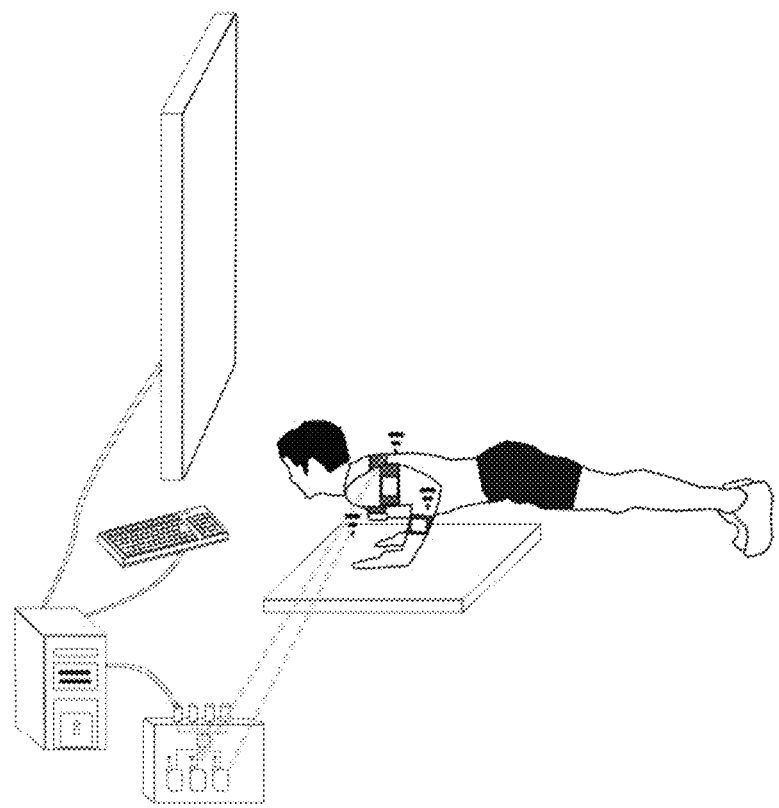
FIG. 2 is a second structural sketch view of the human physical functional ability and muscle ability comprehensive assessment system shown in FIG. 1.

As shown in FIG. 1 and FIG. 2, a human physical functional ability and muscle ability comprehensive assessment system comprises a force measuring system, a motion capture system, a signal collecting system and an information processing system, which is for analyzing and assessing a physical sports ability of a participant.

The muscle quality of the human body can be generally assessed with some muscle characteristics, such as the muscle endurance, the muscle explosiveness and the muscle strength. The joint quality of the human body can be assessed with some joint characteristics, comprising the joint static motion ability and the joint dynamic motion ability. The muscle characteristics and the joint characteristics can be reflected by some factors, such as the movement strength, the movement times, the movement frequency and the movement speed, during the process of completing one fitness movement by one person.

Thus, during the process of completing one fitness movement by the participant, the force measuring system is arranged for measuring the physical quantities related to the used forces of the participant during the process of completing the fitness movement; the motion capture system is arranged for measuring the physical quantities related to the body posture changes of the participant during the process of completing the fitness movement; then the measured data of the physical quantities is collected by the signal collecting system and processed with time synchronization; thereafter, the information processing system extracts and analyzes all of the data; after obtaining multiple characteristic parameters corresponding to the specified fitness movement, the characteristic parameters are classified into multiple parameter sets corresponding to different muscle characteristics or joint characteristics; the data in each parameter set is individually scored and then weighted, so that a composite score for assessing the corresponding muscle characteristic or joint characteristic is obtained.

For example, in the movement of vertical jumping, through obtaining the jumping height, the maximum thrust force to the ground when jumping, the power of vertical jumping, the work, and the explosiveness of the participant, the explosiveness of the lower body of the participant can be analyzed; in the movement of push-up, through obtaining the total thrust force, the maximum thrust force, the average thrust force, the movement times and the movement fatigue points of the arms of the participant, the upper body strength of the participant can be analyzed; in the movement of crunch, through obtaining the movement number, the movement fatigue points and the average bending angle of the participant, the core strength of the participant can be analyzed; in the movement of trunk forward bending, through obtaining the maximum forward bending angle and the time of reaching the maximum angle of the participant, the flexibility of the participant can be analyzed; in the movement of speed walking, through obtaining the speed walking number, the highest frequency, the time of reaching the maximum speed and the duration time at the highest frequency of the participant, the agility of the participant can be analyzed; in the movement of one-leg standing, through obtaining the standing score, the average gravity center shift, the gravity center shift variance and the balance maintaining ratio of the participant, the balance degree of the participant can be analyzed; in the movement of high-knee lift, through obtaining the high-knee lift number, the average frequency, the highest frequency and the time of reaching the highest frequency of the participant, the muscle endurance of the participant can be analyzed.

The individual score means that: according to the statistical data provided by some medical institutions, bodybuilding associations and sports organizations, a great number of the body characteristic parameter values of people with different ages and different genders can be obtained; then according to the big data statistics, a standard is made, and all of the characteristic parameter values in the big data are divided into five different value ranges, namely five regions, respectively corresponding to 1-5 points; for example, the parameter values of most of the people are at a position of 3 points, 30% of the people are at the value ranges of 4 and 5 points, and the rest of the people are at the value ranges of 1 and 2 points.

Particularly, the individual score is obtained through steps of: arranging the obtained N characteristic parameter values from large to small; setting a value of a region from the maximum to 10% to be 5 points; setting a value of a region from 10% to 30% to be 4 points; setting a value of a region from 30% to 70% to be 3 points; setting a value of a region from 70% to 90% to be 2 points; setting a value of a region from 90% to the minimum to be 1 point; and obtaining a correspondence table of different parameter values and different scores. Thereof, when knowing one characteristic parameter value, the corresponding individual score can be found out in the correspondence table.

Figure 3:
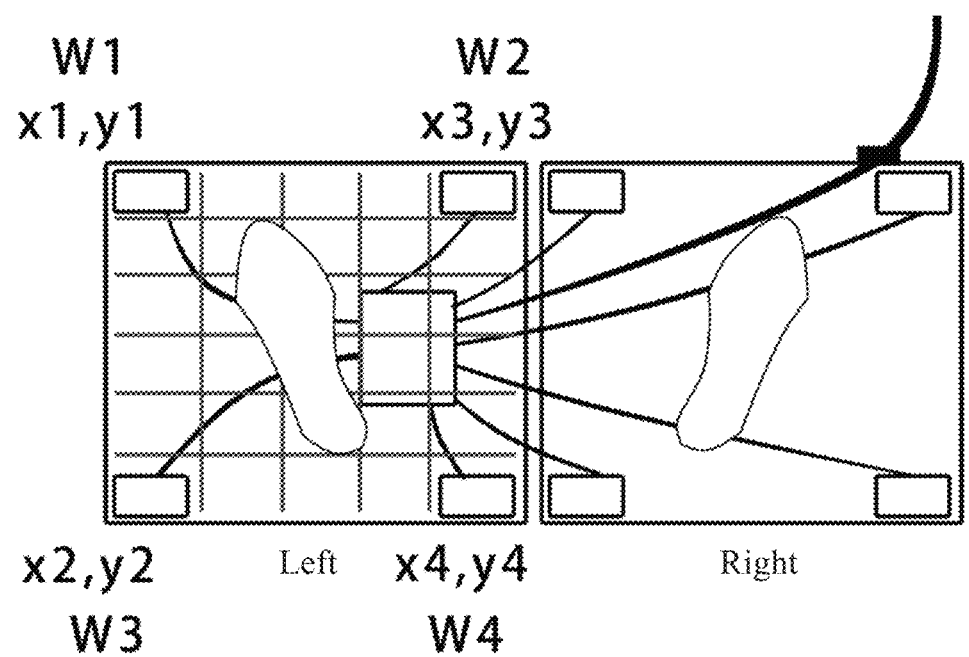
FIG. 3 is a structural sketch view of pressure mats according to the first preferred embodiment of the present invention.
Figure 4:
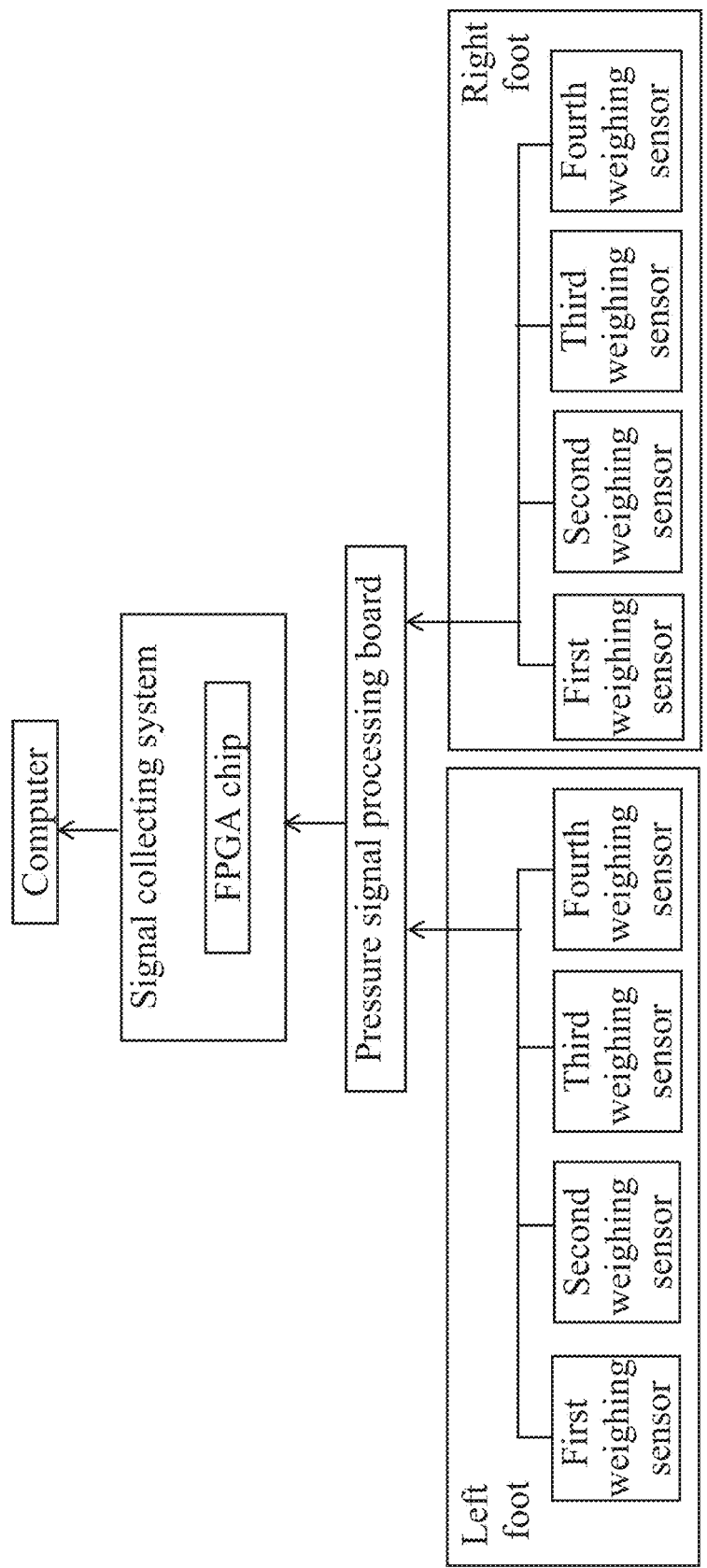
FIG. 4 is a working principle diagram of the pressure mats according to the first preferred embodiment of the present invention.
Figure 5:
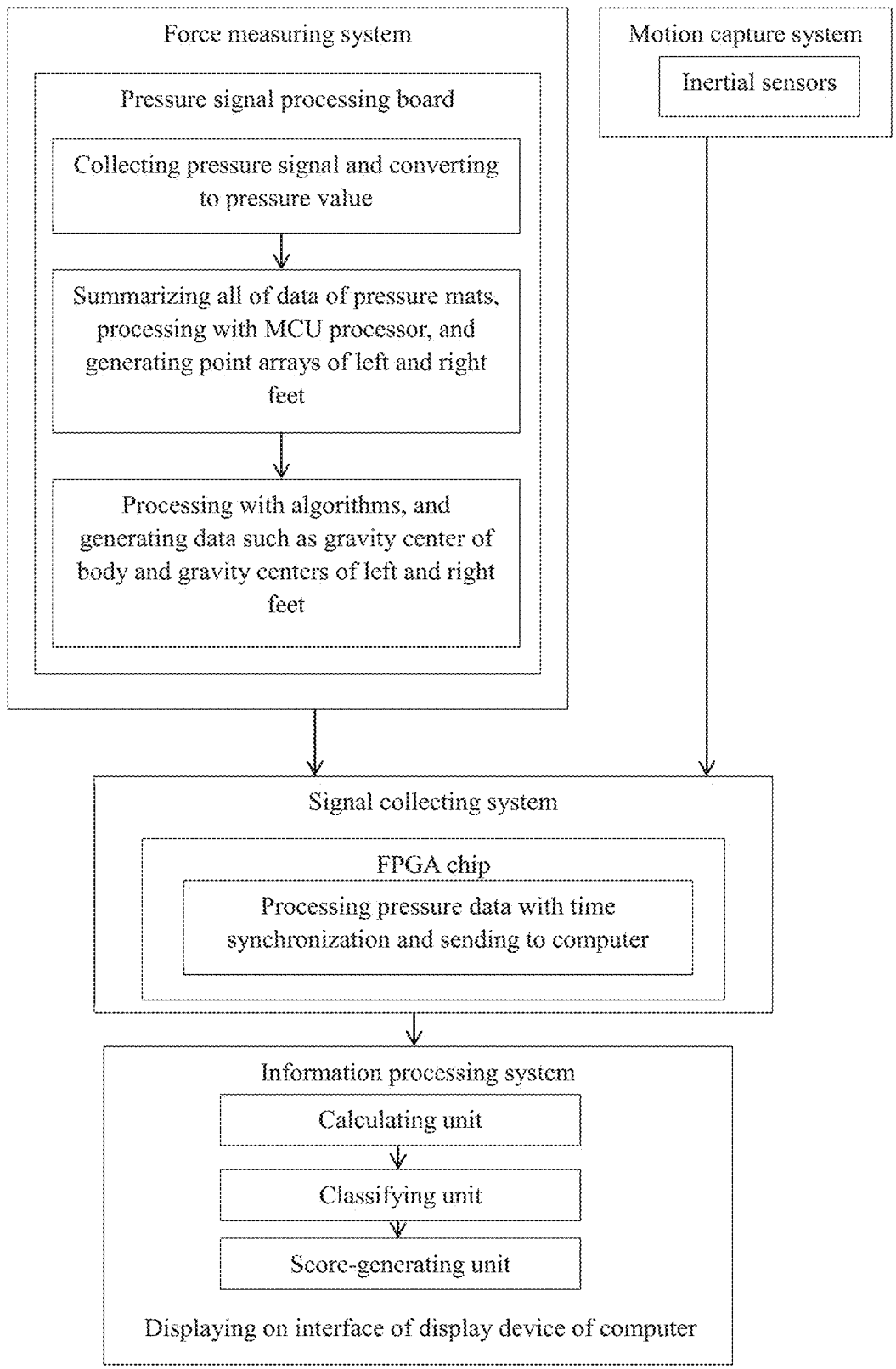
FIG. 5 is a flow diagram of data processing of the pressure mats according to the first preferred embodiment of the present invention.

In order to obtain the characteristic parameters of different fitness movements, referring to FIGS. 3-5, according to the first preferred embodiment, the force measuring system adopts two pressure mats 2; when the participant completes the fitness movement, the body parts act on the pressure mats and generate a thrust force to each pressure mat; each pressure mat is not only able to output the thrust force, but also able to output the position distribution of the thrust force on the pressure mat; the motion capture system adopts three inertial sensors, respectively 5, 6 and 7; through fixing at least two inertial sensors at the moving parts of the participant, the body posture data of the participant is measured.

Particularly, as shown in FIG. 3, the number of the pressure mats is two, and the two pressure mats are arranged in parallel and share the same structure; the pressure mats are rectangular; four weighing sensors, as four pressure collecting points, are respectively arranged at four corners of each pressure mat; a pressure signal processing board is arranged at a center of each pressure mat; a metal cover plate is arranged on the weighing sensors and the pressure signal processing board and is supported by the four weighing sensors; when the person stands on the metal cover plate, the gravity is transmitted to the four pressure collecting points through the metal cover plate, so as to generate the signal changes of the pressure in real-time. An output end of each weighing sensor is connected with the pressure signal processing board; an output end of the pressure signal processing board is connected to the signal collecting system; the pressure signal processing board has an MCU (microcontroller unit) processor; the pressure signal processing board converts the collected pressure signal to the pressure value, summarizes all of the data of the pressure mat (such as the dimension) and then processes with the MCU processor; thereafter, the point arrays of the force-bearing parts of the left and right pressure mats are generated and processed with algorithms, so as to calculate and generate the pressure data, the body gravity center data and the gravity center data of left and right positions. Thereof, when the pressure acts on the metal cover plates, each pressure mat as the independent weighing module can independently output the real-time pressure change, the different distributions of the pressure on the four collecting points and the gravity center position of the pressure; and the two pressure mats can also output simultaneously. For example, for the movement of vertical jumping, through respectively measuring the forces of two legs, the real-time gravity changes of two legs are measured; it is also feasible to measure the pressure gravity center change of one leg when standing by one leg, and which leg is the standing leg can be distinguished.

Figure 7:
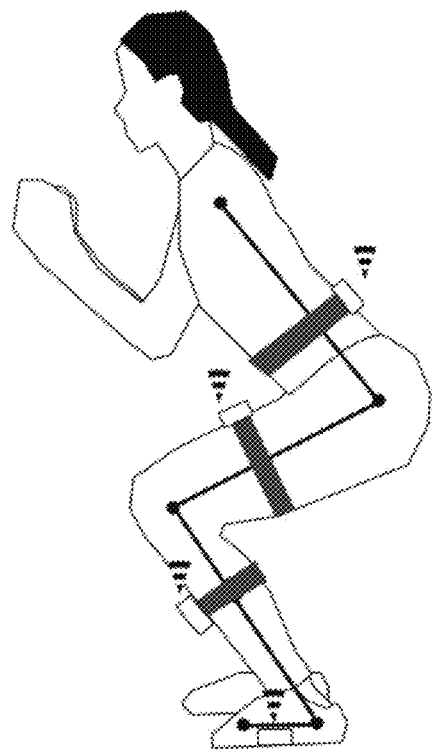
FIG. 7 is a principle diagram of motion capture based on inertial sensors according to the first preferred embodiment of the present invention.

As shown in FIG. 7, each inertial sensor is fixed on an elastic band through the base thereof and then is fastened at one body part through the elastic band. Each inertial sensor comprises an accelerometer, a gyroscope and a digital compass, which is able to measure the acceleration and the angular acceleration related to the posture changes of the human body. Each inertial sensor further comprises an antenna, which is able to wirelessly transmit the measured human body posture data to the signal collecting system.

The signal collecting system 12 comprises multiple signal input interfaces and multiple wireless signal receiving devices 8, 9 and 10. The signal collecting system can collect the pressure data outputted by the force measuring system and the motion trail data wirelessly sent from the multiple inertial sensors at the same time. A central data collecting and processing unit 11 is arranged in the signal collecting system. The central data collecting and processing unit, mainly with the architecture of FPGA (field programmable gate array) chip, is for completing the uniform time synchronization of all the input ends and for completing the synchronous time synchronization of the inputted data. The information processing system 13 adopts a general-purpose computer; the data after the time synchronization is sent to the computer for the uniform algorithm processing. The computer is externally connected with a display device 1 and an input device 14, which are respectively for the interface display and the interaction with the participant.

Figure 8:
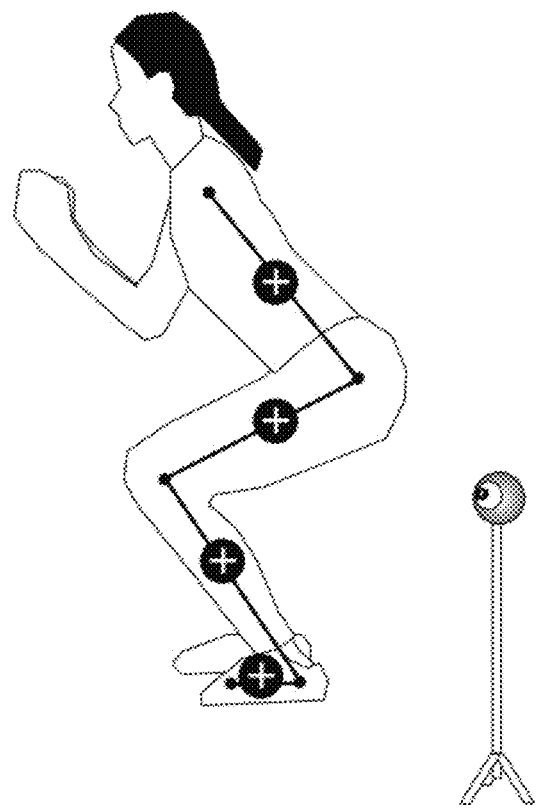
FIG. 8 is a principle diagram of motion capture based on a photographing system combined with visual identification tags according to the first preferred embodiment of the present invention.
Figure 9:
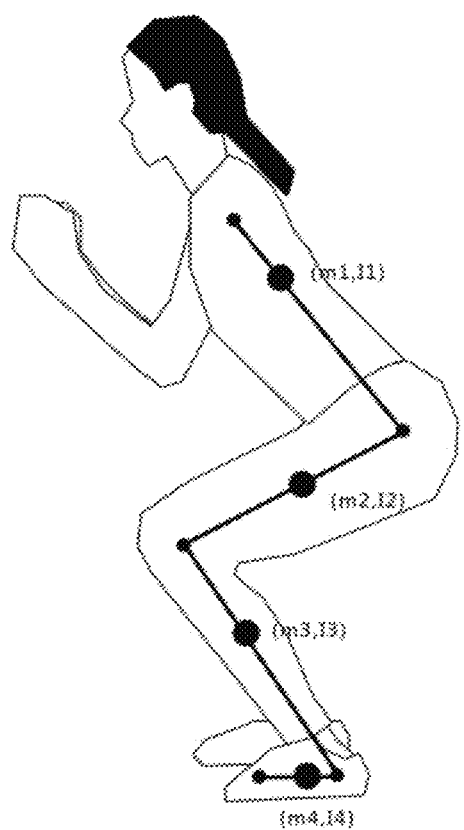
FIG. 9 is a working principle diagram of the inertial sensor according to the second preferred embodiment of the present invention.
Figure 10:
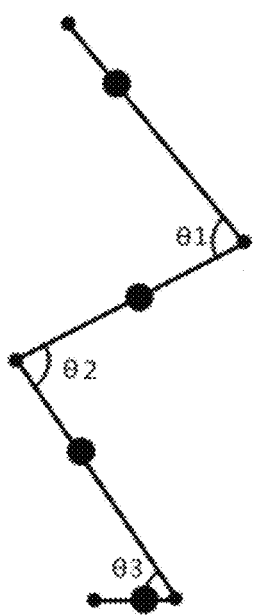
FIG. 10 is a sketch view of a leg bending angle and a waist bending angle shown in FIG. 9.
Figure 11:
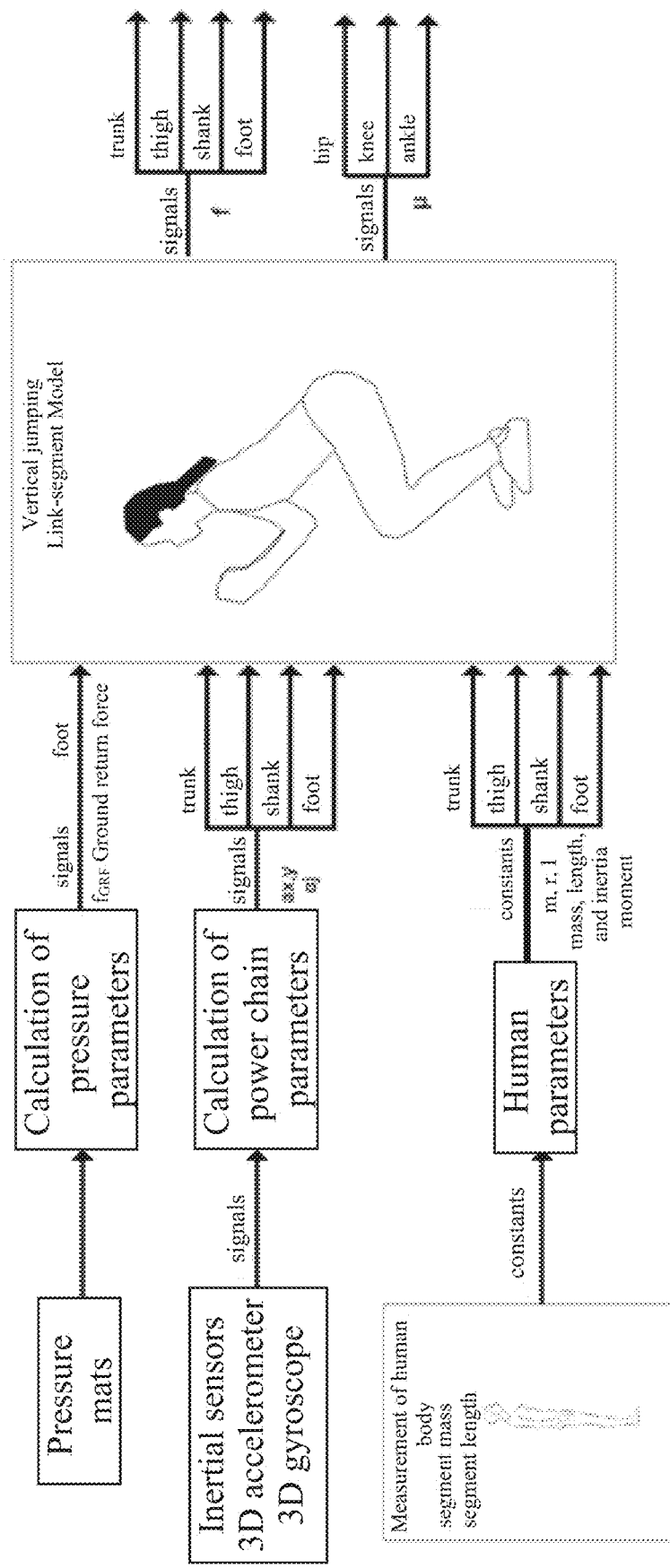
FIG. 11 is a flowchart of processing data measured by the inertial sensors and the pressure mats according to the second preferred embodiment of the present invention.
Figure 12:
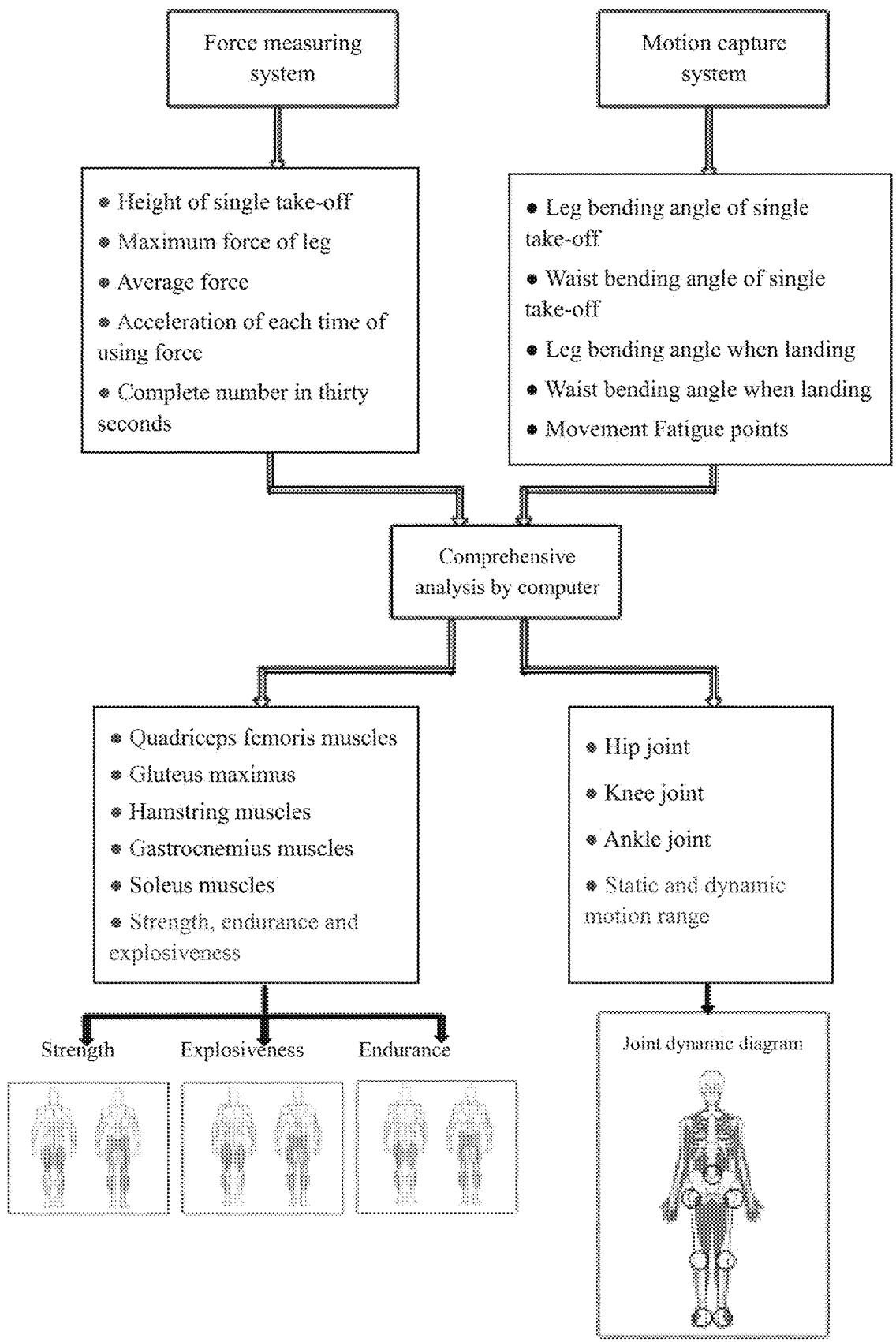
FIG. 12 is a motion analysis diagram of the vertical jumping movement according to the second preferred embodiment of the present invention.

It can be understood that: in some other embodiments, the force measuring system can adopt the pressure mat of other structures; such as the resistance-type pressure mat and the film-type pressure mat, which is able to output the absolute value of the force; the force measuring system can also adopt the biological muscle strength measuring device able to output the absolute value of the muscle contraction force, such as the EMG (electromyography) muscle strength measuring device, or any other device able to reflect the used forces of the muscles of the participant during the process of completing the fitness movement. As shown in FIG. 8, the motion capture system can also adopt at least one photographing system and more than one visual identification tag to serve as the image analysis systems 3 and 4 for capturing the motion attitude images of the human body. The visual identification tag is a plastic or fibrous marker in which a cross or other geometric figure is arranged; the photographing system captures the image with a fixed frame number in one second; with image identification and algorithm analysis, the parameters such as the movement speed, the movement direction and the rotational angular velocity of the visual identification tag are extracted, and the body posture data of the participant is generated, so that merely the related data which describes the spatial position change information of the human body is required to be obtained and not limited herein. Obviously, it is also feasible to know one single characteristic parameter merely with the force measuring system or the motion capture system.

Second Preferred Embodiment

The movement of vertical jumping is taken as an example as follows, and the assessment method based on the human physical functional ability and muscle ability comprehensive assessment system is further described in detail.

Figure 6:
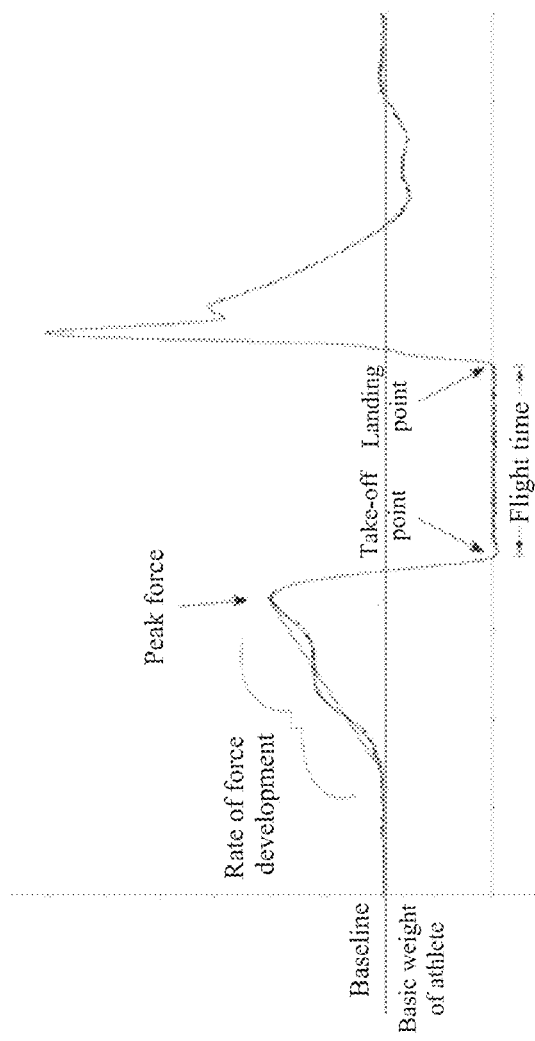
FIG. 6 is a pressure curve diagram of one leg, which is measured by the pressure mat during a movement of vertical jumping, according to a second preferred embodiment of the present invention.
Figure 13:
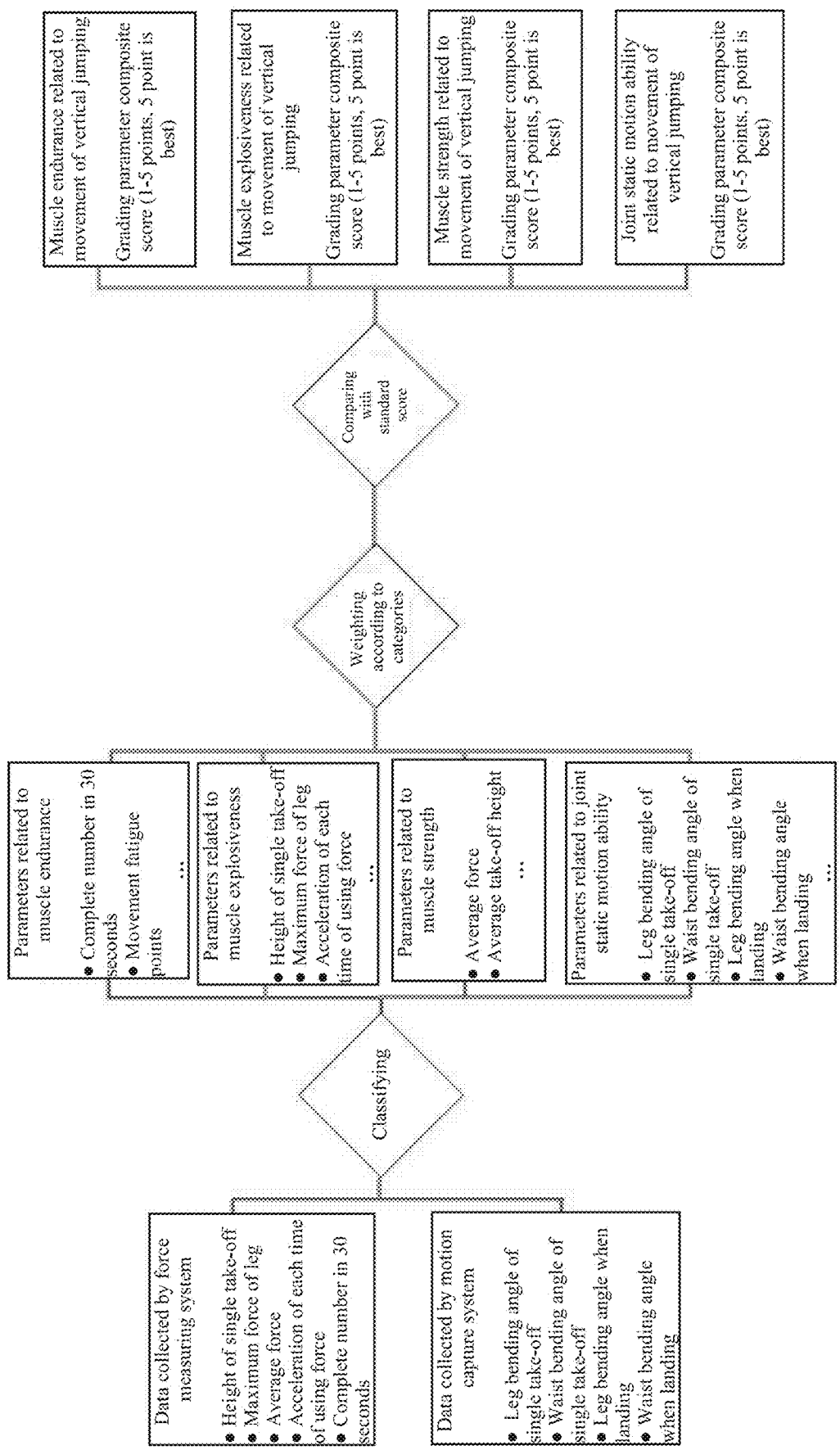
FIG. 13 is a flowchart of classification and calculation of measured data in the movement of vertical jumping according to the second preferred embodiment of the present invention.
Figure 17:
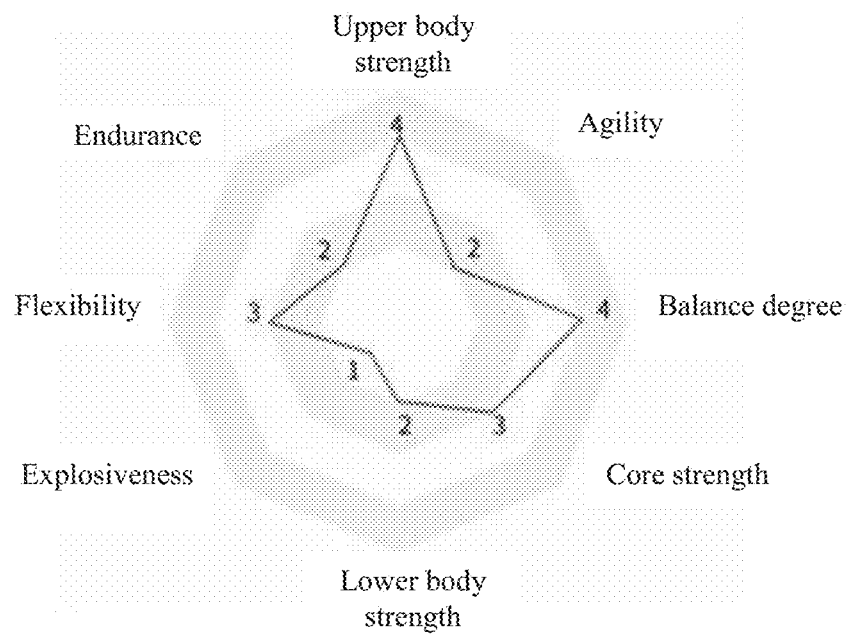
FIG. 17 is a sketch view of a diagram marked with numbers according to the second preferred embodiment of the present invention.

The assessment method comprises steps of:

(1), analyzing and calculating the physical quantities related to the used forces which are measured by the force measuring system, particularly comprising steps of:

(1a), standing on the pressure mats by the participant and completing multiple times of vertical jumping in thirty seconds; wherein for each time of vertical jumping, the weighing sensors at the four corners of each pressure mat transmit the pressure values $W_1$, $W_2$, $W_3$ and $W_4$ of the four points to the corresponding pressure signal processing board;

(1b), completing calculations by the pressure signal processing boards as follows:

calculation of gravity: the gravity of one leg $W_{left}=W_1+W_2+W_3+W_4$; and the total gravity $W_{total}=W_{left}+W_{right}$;

calculation of real-time coordinate positions of gravity centers of two legs: the x-axis coordinate of the gravity center of the left leg $X_{left}=X_i W_i/\Sigma W_i$; and the y-axis coordinate $Y_{left}=Y_i W_i/\Sigma W_i$; and calculation of total gravity center coordinates of the human body: the total x-axis coordinate of the gravity center of the human body $X_{total}=(X_{left}W_{left}+X_{right}W_{right})/W_{total}$; and the total y-axis coordinate $Y_{total}=(Y_{left}W_{left}+Y_{right}W_{right})/W_{total}$;

(1c), transmitting the processed pressure (gravity) and gravity center data to the signal collecting system by the pressure signal processing boards and processing with time synchronization, and then sending the data to the computer; and (1d), according to the movement characteristics of vertical jumping, combined with the pressure curve diagram of one leg which is measured by the pressure mat shown in FIG. 6, obtaining the height of single take-off, the maximum pressure, the average pressure, the acceleration of each time of using the force, and the complete number in thirty seconds of the leg; wherein the related calculation formulas are described as follows:

a) height=½ $g(t/2)^2$, t=Flight Time;

b) maximum thrust force of one leg=pressure value at the point of Peak Force;

c) work=the used force of one leg during the take-off process×take-off time;

d) power=work/take-off time; and e) RFD (rate of force development) of explosiveness=the maximum force change in unit time during the take-off process, namely the maximum acceleration point;

(2), analyzing and calculating the physical quantities related to the body postures which are measured by the motion capture system (referring to FIGS. 9-12), particularly comprising steps of: (2a), during the vertical jumping process of the participant, fastening the inertial sensors respectively at the center of back waist, the thigh, the shank and the ankle of the participant; wherein: each inertial sensor comprises the accelerometer, the gyroscope and the digital compass, which is able to measure the acceleration and the angular acceleration, and able to synchronously analyze the leg bending angle of single take-off, the waist bending angle of single take-off, the leg bending angle when landing, the waist bending angle when landing, and the movement fatigue points;

(2b), calculating the fatigue points in the step (2a), wherein the detailed process is described as follows that:

the fatigue points are divided into the time fatigue points and the strength fatigue points;

the time fatigue points are calculated through collecting the time interval between the repeated same movements; if the used time of one time of movement is longer than the average interval time by 20%, the corresponding time point is called as the time fatigue point;

the strength fatigue points are calculated through the used force or the range of completing the movement; if the strength or the range of completing one time of movement continuously decreases to below 70% of the peak state, the corresponding time point is judged as the strength fatigue point; and both of the time fatigue points and the strength fatigue points are time points, and the point which finally happens at the prior time point is determined as the final fatigue point;

(2c), through the measured ground return force, combined with the measured physical parameters of the upper body, the thigh, the shank and the foot of the human body, namely the mass, length, center of mass (COM) and inertia moment, calculating the force moments of the hip joint, the knee joint and the ankle joint which are connected with the upper body, the trunk, the thigh, the shank and the foot by the reverse dynamic analysis method; wherein the detailed linear equations are described as follows:

$\Sigma F_{x,y}=ma_{x,y}$, wherein: $F_{x,y}$ represents the external force on the horizontal and vertical directions of each joint; m represents the mass of each body part (respectively $m_1$, $m_2$, $m_3$ and $m_4$, which are estimated with the stature); $a_{x,y}$ represents the acceleration on the horizontal and vertical directions which is calculated through the inertial sensor;

$\Sigma M_j=I_j\alpha_j$, wherein $M_j$ represents the force moment generated by $F_{x,y}$; $I_j$ represents the inertia moment of each body part; $\alpha_j$ represents the angular acceleration outputted by the inertial sensor; and $F_{m1}=M_j/B$, wherein B is the force arm from the joint center to the muscle force direction; the calculated $F_{m1}$ reflects the used force of the related muscles of each joint, namely the muscle strength corresponding to the different joints; in a similar way, $F_{m2}$, $F_{m3}$ and $F_{m4}$ can be calculated;

(3), extracting the characteristic parameters, classifying and calculating the parameter composite scores (referring to FIG. 12), particularly comprising steps of:

(3a), after finishing collecting the above series of data by the force measuring system and the motion capture system, through classification and calculation of the information processing system, forming a series of original data and calculation data sets;

(3b), extracting some parameters from the above parameter sets to serve as the characteristic parameters of the vertical jumping movement, comprising the height of single take-off, the maximum force and the average force of the leg, the acceleration of each time of using the force, the complete number in thirty seconds, the leg bending angle of single take-off, the waist bending angle of single take-off, the leg bending angle when landing, the waist bending angle when landing, and the movement fatigue points;

(3c), classifying the characteristic parameters of the vertical jumping movement into parameter sets of four dimensions, respectively a parameter set related to the muscle endurance (comprising the complete number in thirty seconds and the movement fatigue points), a parameter set related to the muscle explosiveness (comprising the height of single take-off, the maximum force of leg, and the acceleration of each time of using the force), a parameter set related to the muscle strength (comprising the average force and the average take-off height), and a parameter set related to the joint static motion ability (comprising the leg bending angle of single take-off, the waist bending angle of single take-off, the leg bending angle when landing, and the waist bending angle when landing); and (3d), individually scoring each parameter in the parameter sets of four dimensions and then weighting according to a relevancy to the four dimensions of muscle endurance, muscle explosiveness, muscle strength and joint motion ability, so that the parameter composite scores (namely the weighted scores) of the vertical jumping movement on the four dimensions are obtained; wherein: because the movement of vertical jumping corresponds to a specified muscle group of quadriceps femoris muscles, gluteus maximus, hamstring muscles, gastrocnemius muscles and soleus muscles, the parameter composite scores can reflect the ability of the above specified muscle group of the participant; because the movement of vertical jumping also corresponds to the hip joints, the knee joints and ankle joints, the parameter composite scores can also reflect the ability of the specified joints;

(4), grading the parameter composite scores into different levels and obtaining diagrams (referring to FIG. 13), particularly comprising steps of:

(4a), setting a standard score (namely the weighted score) which represents the normal human body, or obtaining an average statistical score (namely the weighted score) of the same age group to serve as the standard score;

(4b), comparing the parameter composite scores obtained in the step (3) with the standard score and then grading, wherein: there are five levels; 5 points represents the best and 1 point represents the worst; through grading with five scores of 1-5, the muscle quality and the joint quality of the specified muscle group and joint of the participant can be assessed; and (4c), according to the parameter composite scores of the muscle characteristics and joint characteristics or the levels thereof, forming the muscle characteristic diagrams and the joint characteristic diagrams; wherein: in the muscle characteristic diagrams, the muscle ability of the specified muscle groups is represented by different colors; in the joint characteristic diagrams, the joint ability of the specified joint can be also represented by different colors; with the diagrams, the positions and strength of the specified muscle groups and joints can be directly obtained on the display device, so that the participant, the coach and the doctor can know the muscle ability and health state of the participant easily according to the diagrams, which is convenient for the athletes, the coach and the doctor to make the targeted training and repeatedly check the training results; obviously, in some other embodiments, the diagrams can be formed through the method of directly marking the level numbers as shown in FIG. 17, and any other method which can reflect the relative differences is adoptable and not limited herein.

Third Preferred Embodiment

Six fitness movements as examples are described as follows, so as to help to understand the realization of a comprehensive assessment method.

(1) Push-Up

Figure 14:
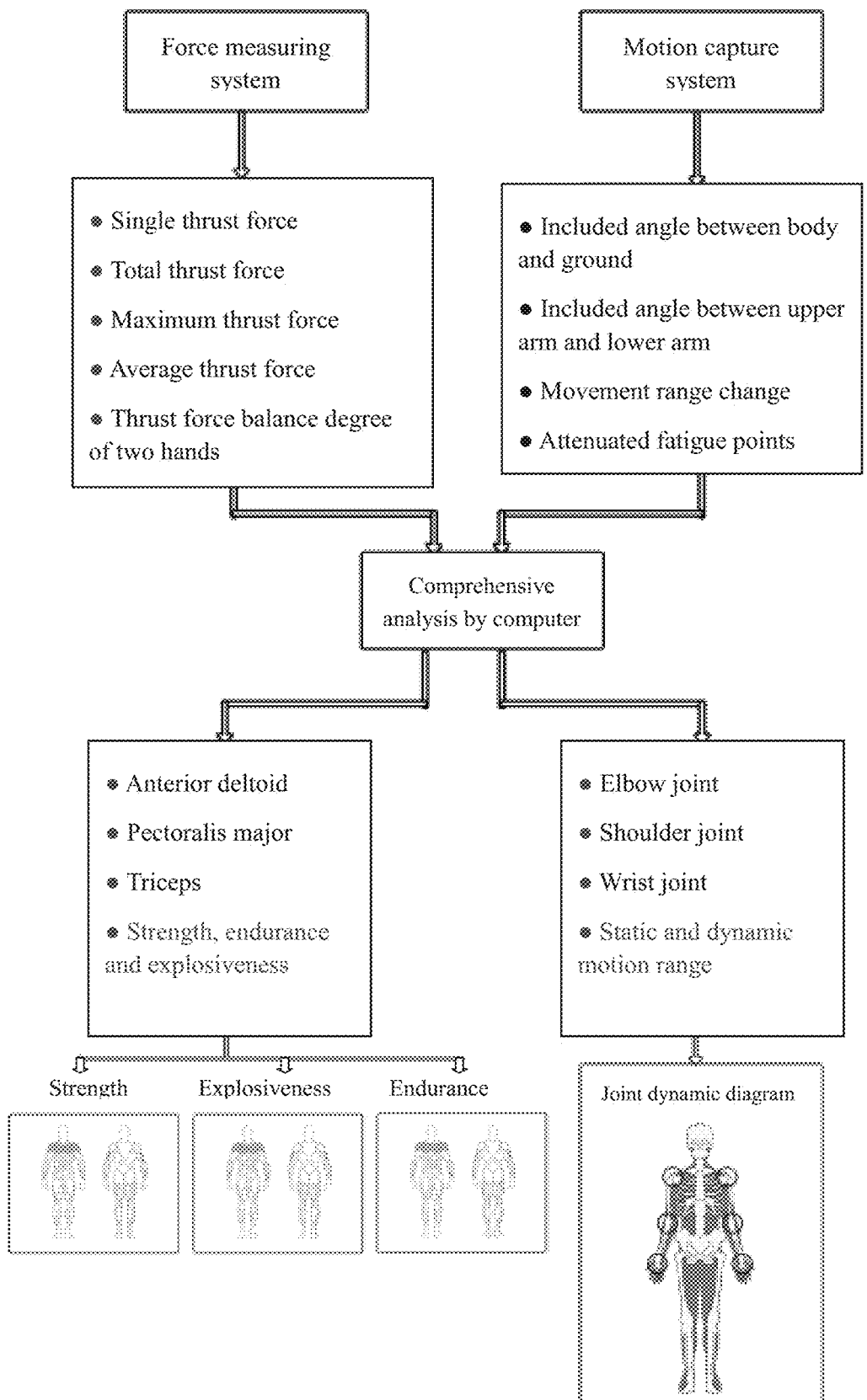
FIG. 14 is a motion analysis diagram of a movement of push-up according to a third preferred embodiment of the present invention.

The inertial sensors are respectively arranged at the chest, the upper arm and the lower arm of the participant, and meanwhile the participant props the two hands on the pressure mats for uninterruptedly making the push-up movement in sixty seconds. The pressure mats can accurately analyze the single thrust force, the total thrust force, the maximum thrust force, the average thrust force and the thrust force balance degree of two hands of the user; the inertial sensors can synchronously analyze the included angle between the body and the ground, the included angle between the upper arm and the lower arm, the movement range change and the attenuated fatigue points of single movement. Referring to FIG. 14, the muscles related to the movement of push-up comprise the anterior deltoid, the pectoralis major and the triceps, and the joints related to the movement of push-up comprise the elbow joints, the shoulder joints and the wrist joints, so that the ability of the specified muscle groups and joints related to the movement of push-up of the participant can be comprehensively and accurately judged with the data.

The calculation formulas related to the parameter calculation of the movement of push-up are described as follows:

a) total thrust force=$\Sigma p$, p=single thrust force of two hands;

b) maximum thrust force=a maximum force value in the single thrust force;

c) fatigue point=the first time of lower than 75% of the last peak value during the movement process;

d) average thrust force=$\Sigma p/n$, wherein n is the number of push-ups; and e) number=n, wherein n is the number of push-ups.

(2) Crunch

The inertial sensors are respectively arranged at the thigh, the center of back waist and the center of chest of the participant, and meanwhile the hip of the participant sits on the pressure mat for uninterruptedly making the crunch movement. Through the pressure mat and the inertial sensors, the crunch number, the movement fatigue points and the average bending angle of the user can be accurately analyzed. Because the muscles related to the movement of crunch are mainly the abdominal muscles, the abdominal core strength of the participant can be judged with the data.

The calculation formulas related to the parameter calculation of the crunch movement are described as follows:

a) number=n, wherein n is the number of crunches;

b) fatigue point=the first time of lower than 75% of the last peak value during the movement process; and c) average bending angle=$\Sigma x/n$, x=angle of single crunch.

(3) Trunk Forward Bending

The inertial sensors are arranged at the thigh and the center of back waist of the participant, and meanwhile the participant stands on the pressure mats with two legs for making the trunk forward bending movement. Through the pressure mats and the inertial sensors, the maximum forward bending angle and the time of reaching the maximum angle of the user can be accurately analyzed. The muscles related to the movement of trunk forward bending are mainly the spinal erector muscles, the leg muscles and the gastrocnemius muscles, and the joints related to the movement of trunk forward bending are mainly the hip joints, so that the ability of the specified muscle groups and joints related to the movement of trunk forward bending of the participant can be accurately judged with the data.

The calculation formulas related to the parameter calculation of the movement of trunk forward bending are described as follows:

a) maximum forward bending angle=an achievable maximum angle of holding for more than three seconds; and b) time of reaching the maximum angle=a used time to reach the maximum forward bending angle.

(4) Speed Walking

The inertial sensors are respectively arranged at the center of back waist, the thigh and the ankle of the participant and the participant makes a fast walking movement. Through the inertial sensors, the number of speed walking, the highest frequency, the time of reaching the maximum speed and the duration time at the highest frequency of the user can be accurately analyzed. The muscles related to the speed walking movement are mainly the hip flexor muscles, the quadriceps femoris muscles and the plantar flexor muscles, and the joints related to the speed walking movement are mainly the knee joints, so that the ability of the specified muscle groups and joints related to the speed walking movement of the participant can be accurately judged with the data.

The calculation formulas related to the parameter calculation of the speed walking movement are described as follows:

a) number=n, wherein n is the sum speed walking number of two feet;

b) highest frequency=f, wherein f is the reachable largest number in one second;

c) time of reaching the maximum speed=a used time to reach the highest frequency; and d) duration time at the highest frequency=time of holding at the highest frequency.

(5) One-Leg Standing

The participant stands on the pressure mats with two feet and alternately lifts one foot for making the one-leg standing movement. Through the pressure mats, the balance score of one foot, the average gravity center shift, the gravity center shift variance and the balance maintaining ratio can be accurately analyzed. Because the muscles related to the one-leg standing movement are mainly the quadriceps femoris muscles, the ability of the specified muscle groups related to the one-leg standing movement of the participant can be accurately judged with the data.

The calculation formulas related to the parameter calculation of the one-leg standing movement are described as follows:

a) balance score: dividing into four levels according to the circle center deviation degree, wherein the nearest is 4 points and the farthest is 1 point; total score=Σ(score corresponding to each sampling gravity center $G_i$);

b) average gravity center shift=Σ(each sampling gravity center $G_i$–original gravity center $G_0$)/sampling number n;

c) gravity center shift variance=Σ$(G_i-G_0)^2$/sampling number n; and d) balance maintaining ratio=Σs*t/30, wherein s represents a single score and t is a duration time of the score.

(6) High-Knee Lift

The inertial sensors are respectively fastened at the center of back waist, the thigh, the shank and the ankle of the participant, and the participant stands on the pressure mats with two feet. Through the pressure mats and the inertial sensors, the movement number, the average frequency, the highest frequency and the time of reaching the highest frequency of the user can be accurately analyzed. The muscles related to the high-knee lift movement comprise the quadriceps femoris muscles, the gluteus maximus, the gastrocnemius muscles and the soleus muscles, and the joints related to the high-knee lift movement comprise the hip joints and the knee joints, so that the ability of the specified muscle groups and joints related to the high-knee lift movement of the participant can be accurately judged with the data.

The calculation formulas related to the parameter calculation of the high-knee lift movement are described as follows:

a) average frequency=total movement number/total movement time;

b) highest frequency=a reachable largest number in one second;

c) time of reaching the highest frequency=a used time to reach the highest frequency; and d) average knee lifting angle=Σangle/n, wherein angle is the angle of each movement; and n is the movement number.

Figure 15:
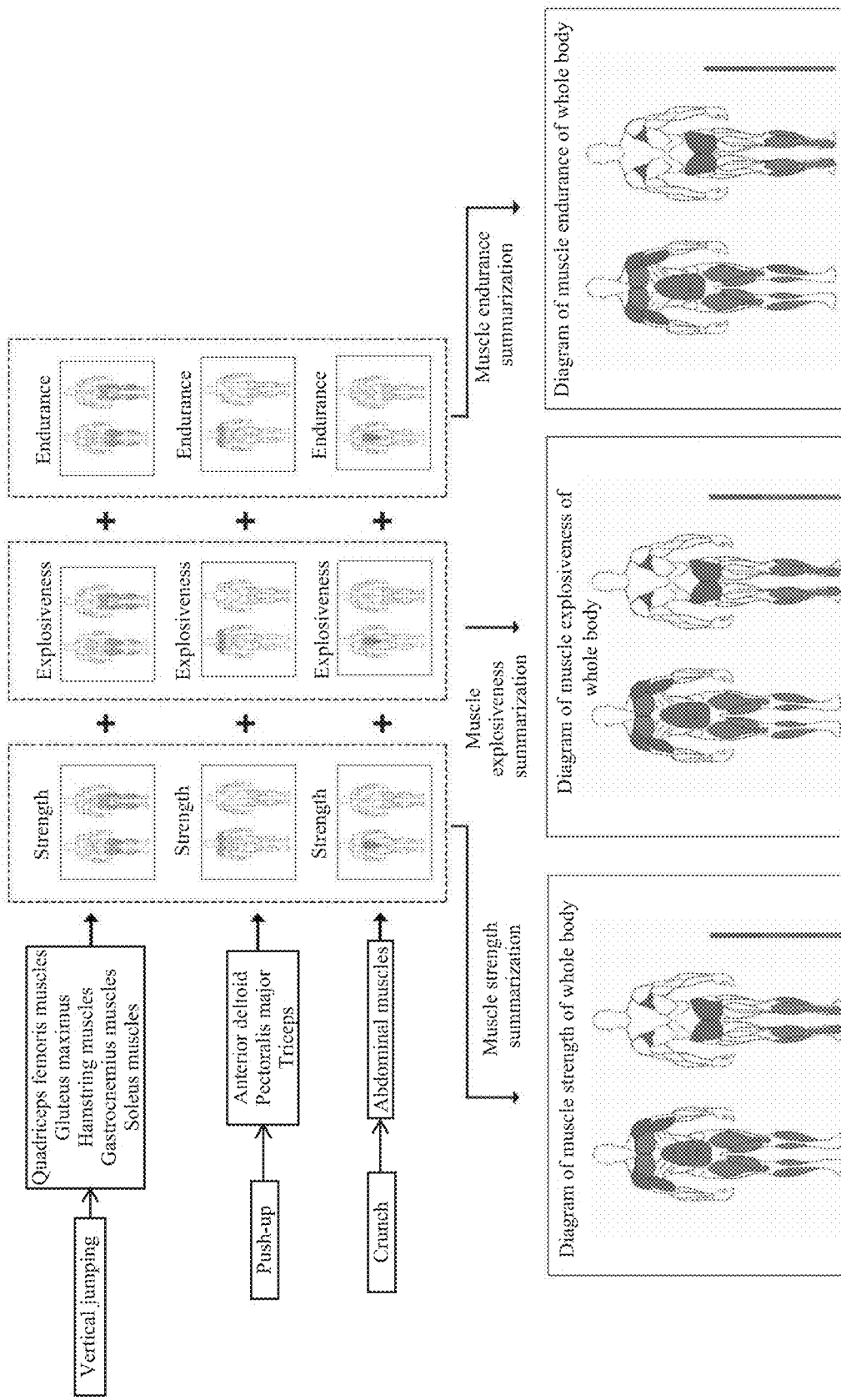
FIG. 15 is a muscle three-dimensional diagram formed by measurement of multiple movement combinations according to the third preferred embodiment of the present invention.
Figure 16:
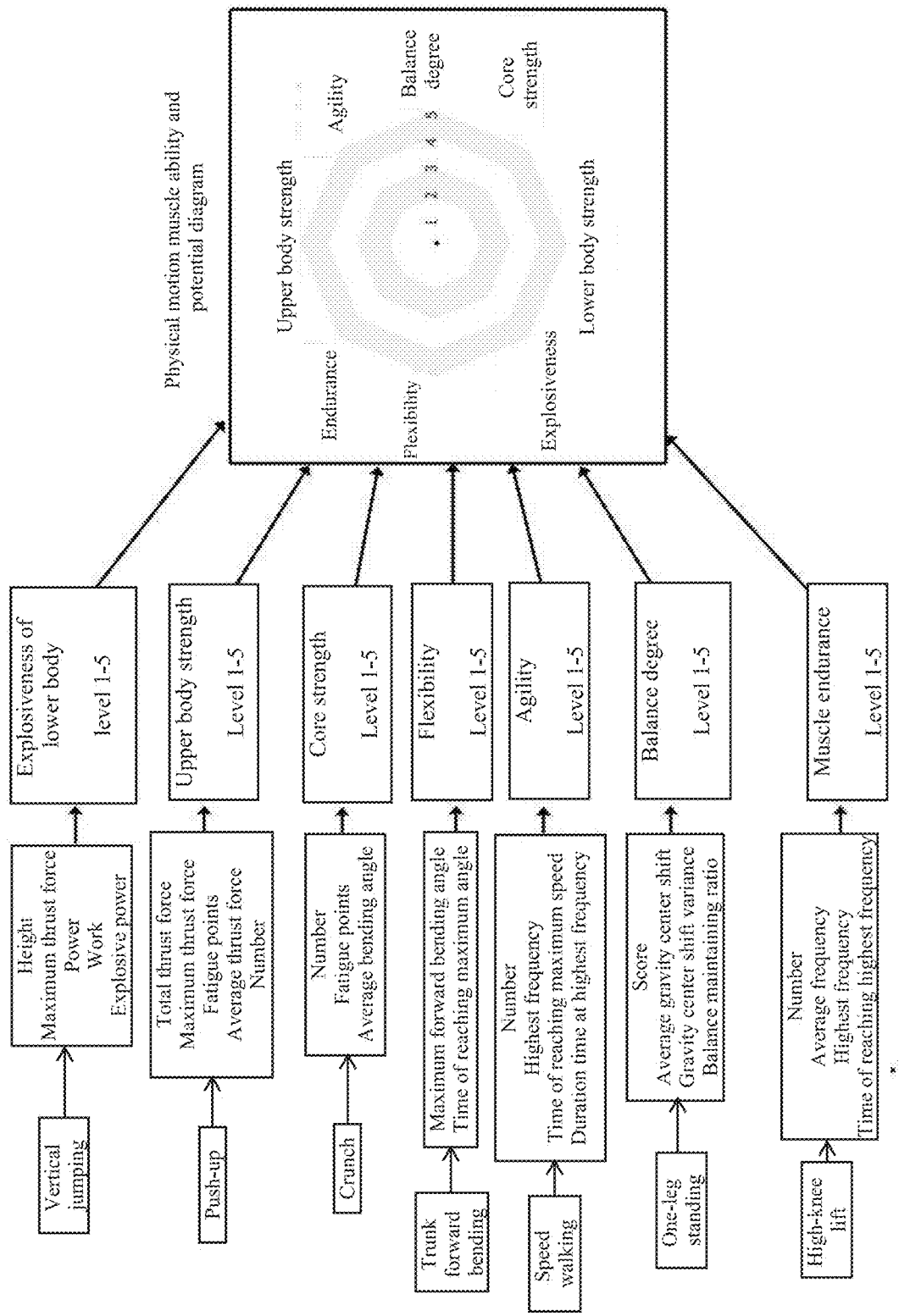
FIG. 16 is a physical dynamic ability diagram formed by the measurement of the multiple movement combinations according to the third preferred embodiment of the present invention.

Referring to FIG. 15 and FIG. 16, based on the above multiple fitness movements covering the main muscles of the whole body or the muscles of target regions, through completing a movement combination comprising multiple movements by the participant, such as the above seven fitness movements, an array of related data about the physical dynamic ability is calculated, covering the upper and lower body strength, the core strength, the lower body explosiveness, the flexibility, the agility, the balance degree, the muscle endurance and so on, so that the sports ability and the fitness degree of one person can be quickly assessed. The obtained four-dimensional data about the muscles and joints basically covers the ability of the large muscle groups and main joints of the whole body, and a whole set of muscle characteristic and joint characteristic diagrams of the whole body are finally formed, so that the characteristic analysis of multiple muscle groups and joints of the whole body can be obtained more conveniently and more quickly, the time is greatly saved compared with the traditional analysis method, and the generated series diagrams are more scientific and more accurate.

For example, the measurement of the explosiveness and strength of the lower body is completed through continuous vertical jumping, and the related measurement results comprise the thrust force of two legs, the explosiveness of two legs, and the muscle balance degree of two legs. The upper body strength is measured through completing the push-up movement in a given time, and the measurement results comprise the total thrust force, the average thrust force, the maximum thrust force, the fatigue points and the complete number. The core strength is measured through completing the crunch movement in a given time, and the measurement results comprise the complete number, the fatigue points and the average bending angle. The flexibility is measured through completing the simple movement of standing trunk forward bending, and the related measurement results comprise the forward bending angle and the time of reaching the maximum angle. The agility is measured through completing the speed walking movement in a given time, and the measurement results comprise the complete number, the highest frequency, the time of reaching the highest frequency and the duration time at the highest frequency. The balance degree is measured through completing the one-leg standing movement in a given time, and the measurement results comprise the balance score, the average gravity center shift, the gravity center shift variance and the balance maintaining ratio. The muscle endurance is measured through completing the high-knee lift movement in a given time, and the measurement results comprise the complete time, the highest frequency, the time of the reaching the highest frequency and the duration time at the highest frequency. Through the measurement of above seven movements, a parameter matrix for assessing the physical comprehensive sports ability (comprising seven aspects of lower body explosiveness, lower body strength, core strength, flexibility, agility, balance degree, and muscle endurance) of the participant is finally obtained. The parameter sets of the measurements above are graded into five levels (respectively need improvement, average, above average, very good and excellent) through comparing with the standard or with the statistical data of the same age group; with two or more fitness movements, at least one parameter of each movement is extracted, analyzed and graded, so that a level assessment and a score of the physical comprehensive sports ability of one person is finally formed.

It is understandable that: in some other embodiments, through completing other fitness movements, the muscle characteristic analysis of other muscle groups and the joint characteristic analysis of other joints can be independently obtained; it is also feasible to obtain the muscle characteristic analysis and the joint characteristic analysis of muscle groups and joints at other parts at the same time.

Fourth Preferred Embodiment

Figure 18:
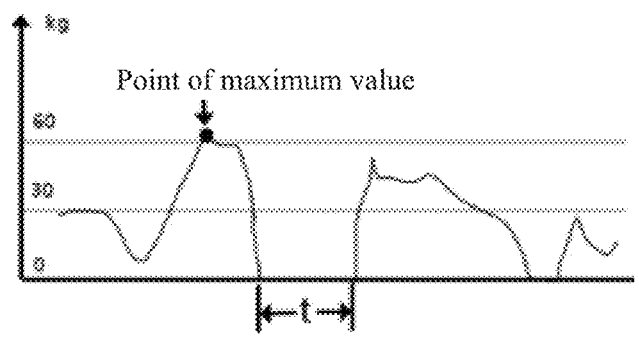
FIG. 18 is a pressure curve diagram measured by the pressure mat according to a fourth preferred embodiment of the present invention.

The movement of vertical jumping is taken as an example, and the detailed data calculation flow of the comprehensive assessment method is described as follows, comprising steps of:

(1), selecting a healthy male of nineteen years old with a height of 176 cm and a weight of 65 kg; fastening the inertial sensors respectively at the upper body, the thigh, the shank, and the instep; wherein the participant stands on the pressure mats with two feet, and the participant makes the vertical jumping movement with arms akimbo, so as to avoid the physical effects caused by arm waving;

(2), obtaining the parameter composite score of the muscle explosiveness (namely the lower body strength), particularly comprising steps of:

(2a), calculating the characteristic parameter values with an output pressure curve of the pressure mat shown in FIG. 18, wherein: related calculation formulas are described as follows:

a) height=½ g(t/2)², t=4.7979 s, height=28.2 cm;
  b) maximum thrust force of one foot=60.28*9.8=590.7 N;
  c) work=used force of one foot during the take-off process×take-off time=237.05 J;
  d) power=237.05 J/152.94=1.55 HP; and
  e) RFD of explosiveness=288.69 N/s;

(2b), comparing the calculated five characteristic parameter values with the standard table, and obtaining an individual score of each characteristic parameter value; weighting the obtained individual scores of all the characteristic parameter values, as shown in Table 1, and obtaining a score of 2.8 after weighting; and

TABLE 1

| | Parameter | Individual score | Weighting factor |
|---|---|---|---|
| Height | 28.2 | 3 | 0.6 |
| Maximum thrust force | 590.7 | 3 | 0.2 |
| Walk | 237.05 | 2 | 0.05 |
| Power | 1.55 | 2 | 0.05 |
| RFD | 288.69 | 2 | 0.1 |
| Weighted score | | | 2.8 |

(2c), according to Table 2, directly obtaining that the level of the composite score of the muscle explosiveness of the lower body strength of the male is 2 when the weighted score is 2.8, wherein Table 2 shows the statistical grading standard of the weighted score of the group with the same age group and the same gender;

TABLE 2

| | Age group of 0-35 years old | | | | |
|---|---|---|---|---|---|
| | 5 | 4 | 3 | 2 | 1 |
| Weighted score | 4.5-5.0 | 3.8-4.5 | 2.9-3.8 | 1.8-2.9 | 1-1.8 |

Figure 19A:
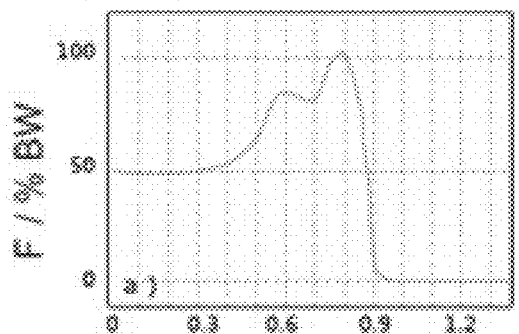
FIG. 19(a) is a curve diagram of a percentage of a used force of muscles related to an ankle joint to weight, which is measured by the inertial sensor, according to the fourth preferred embodiment of the present invention.
Figure 19B:
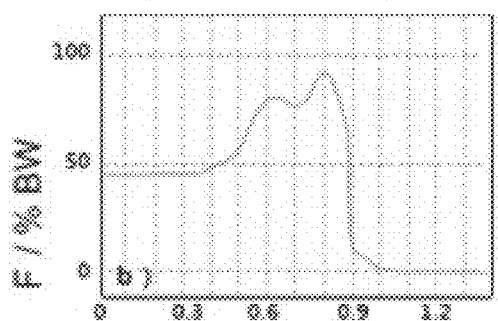
FIG. 19(b) is a curve diagram of a percentage of a used force of muscles related to a knee joint to weight, which is measured by the inertial sensor, according to the fourth preferred embodiment of the present invention.
Figure 19C:
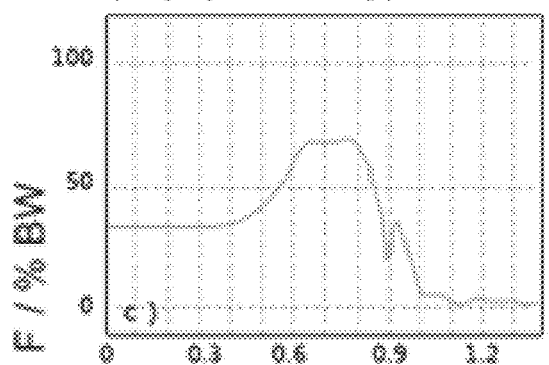
FIG. 19(c) is a curve diagram of a percentage of a used force of muscles related to a hip joint to weight, which is measured by the inertial sensor, according to the fourth preferred embodiment of the present invention.
Figure 20A:
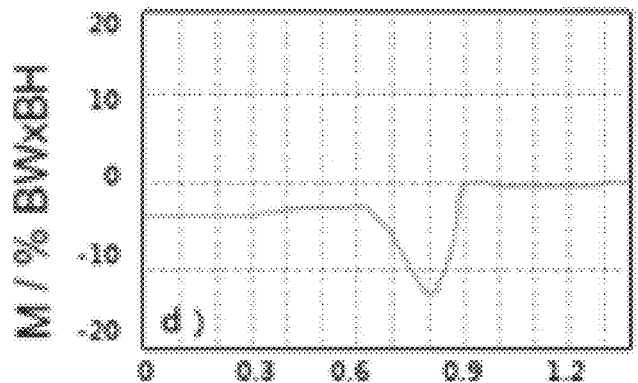
FIG. 20(a) is a curve diagram of an ankle force moment during a take-off process corresponding to FIG. 19(a).
Figure 20B:
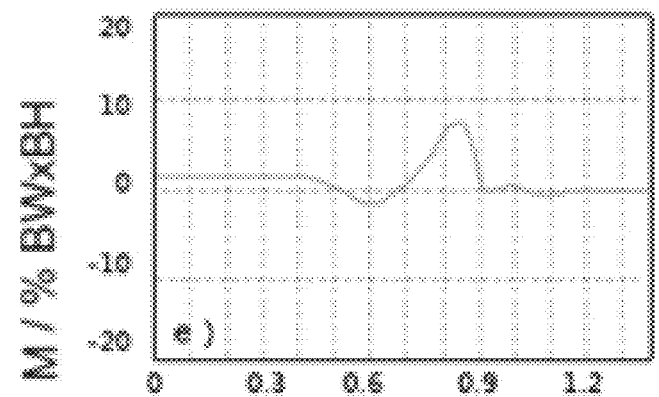
FIG. 20(b) is a curve diagram of a knee force moment during the take-off process corresponding to FIG. 19(b).
Figure 20C:
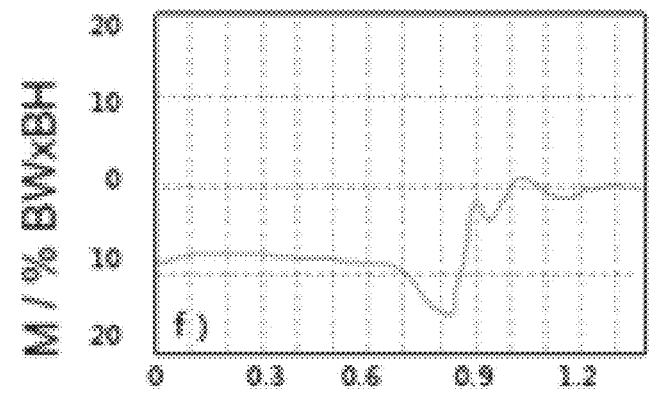
FIG. 20(c) is a curve diagram of a hip force moment during the take-off process corresponding to FIG. 19(c).

(3), obtaining the parameter composite score of the muscle strength, particularly comprising steps of:

(3a), measuring the length and latitude of the upper body, the thigh and the shank of the male body; calculating the mass center and inertia moment of each inertial sensor; inputting the output values of the inertial sensors and the ground pressure mats into the linear equations of $\Sigma F_{x,y}=ma_{x,y}$ and $\Sigma M_j=I_j\alpha_j$; obtaining the percentage of the external forces of the ankle joint, the knee joint and the hip joint corresponding to the jumping height to the weight, as shown in FIGS. 19(a), 19(b) and 19(c); obtaining the percentage of the force moments of the ankle joint, the knee joint and the hip joint to the weight, as shown in FIGS. 20(a), 20(b) and 20(c); after multiplying by the weight, obtaining the maximum external force and force moment can be understood by the three joints shown in Table 3 from the FIGS. 19(a)-(c) and FIGS. 20(a)-(c);

TABLE 3

| Force of ankle joint $F_{ankle\_max}$ | Force of knee joint $F_{knee\_max}$ | Force of hip joint $F_{hip\_max}$ |
|---|---|---|
| 643.37 | 579.67 | 433.16 |

| Force moment of ankle joint $M_{ankle\_max}$ | Force moment of knee joint $M_{knee\_max}$ | Force moment of hip joint $M_{hip\_max}$ |
|---|---|---|
| 134.53 | 71.75 | 159.2 |

(3b), according to the formula of $F_{m1}=M_j/B$, calculating the maximum force of the lower leg muscle group, the quadriceps femoris muscle group, and the gluteus maximus group corresponding to each joint during the take-off process, as shown in Table 4; and

TABLE 4

| First force arm B1 | Second force arm B2 | Third force arm B3 |
|---|---|---|
| 5 | 6 | 10 |
| Force of lower leg muscle group $F_{LMG}$ | Force of quadriceps femoris muscle group $F_{QFMG}$ | Force of gluteus maximus group $F_{GMG}$ |
| 2691 | 1196 | 1592 |

(3c), comparing the results in Table 4 with the statistical reference values of the corresponding muscle groups, and obtaining the parameter composite scores of the muscle strength corresponding to the above muscles of the male (referring to the method of obtaining the composite score of the muscle explosiveness), as shown in Table 5;

TABLE 5

|  | Name of corresponding muscles | Score |
|---|---|---|
| Lower leg muscle group | Soleus muscle and gastrocnemius muscle | 2 |
| Quadriceps femoris muscle group | Quadriceps femoris muscle | 3 |
| Gluteus maximus group | Gluteus maximus and hamstring muscle | 3 |

(4), obtaining the parameter composite score of the muscle endurance, particularly comprising steps of:

(4a), performing a non-stop continuous jumping on the pressure mats by the male participant; according to the force peak number of the pressure curve, obtaining that the completed jumping number in thirty seconds is 20; analyzing the force of each muscle group of 20 times of jumping; when the force of one jump is lower than 70% of the peak force observed, obtaining the fatigue points of each muscle group, as shown in Table 6; and

TABLE 6

|  | Fatigue point (number) |
|---|---|
| Lower leg muscle group | 12 |
| Quadriceps femoris muscle group | 16 |
| Gluteus maximus group | 18 |

(4b), comparing the results with the statistical reference values of the corresponding muscle groups, and obtaining the composite scores of the muscle endurance corresponding to the above muscles of the male (referring to the method of obtaining the composite score of the muscle explosiveness), as shown in Table 7;

TABLE 7

|  | Name of corresponding muscles | Score |
|---|---|---|
| Lower leg muscle group | Soleus muscle and gastrocnemius muscle | 2 |
| Quadriceps femoris muscle group | Quadriceps femoris muscle | 3 |
| Gluteus maximus group | Gluteus maximus and hamstring muscle | 4 |

(5), obtaining the parameter composite score of the joint static motion ability, particularly comprising steps of:

(5a), making statistics of the minimum angles of the waist (namely the included angle between the upper body and the thigh), the knee (namely the included angle between the thigh and the shank), and the ankle (namely the included angle between the shank and the sole) of 20 times of jumping when taking-off and landing, and obtaining the average joint motion range, as shown in Table 8; and

TABLE 8

|  | Minimum angle of waist $Angle_{waist\_min}$ | Minimum angle of knee $Angle_{knee\_min}$ | Minimum angle of ankle $Angle_{ankle\_min}$ |
|---|---|---|---|
| Angle when taking-off (°) | 75 | 92 | 67 |
| Angle when landing (°) | 70 | 88 | 62 |
| Average angle (°) | 72.5 | 90 | 64.5 |

(5b), comparing the results with the statistical reference values of the joint motion range, and obtaining the composite scores of the motion ability corresponding to the above joints of the male (referring to the method of obtaining the composite score of the muscle explosiveness), as shown in Table 9;

TABLE 9

|  | Score |
|---|---|
| Waist | 2 |
| Knee joint | 3 |
| Ankle joint | 4 | through the above steps, the parameter composite scores of the muscle endurance, the muscle explosiveness, the muscle strength and the joint static motion ability related to the movement of vertical jumping are obtained.

The above-described is merely the preferred embodiments of the present invention and not for limiting the range of the present invention. Any equivalent structure change derived from the specification and accompanying drawings of the present invention without departing from the spirit of the present invention, or any direct/indirect application of the present invention in other related technical fields are all encompassed in the protection range of the present invention.

What is claimed is:

1. A human physical functional ability and muscle ability comprehensive assessment method with a human physical functional ability and muscle ability comprehensive assessment system, wherein: the system comprises a force measuring system, a motion capture system, a signal collecting system and an information processing system which is a computer;

the method comprises steps of:

(S1), during a process of completing a fitness movement by a participant, measuring physical quantities related to used forces through the force measuring system, and/or measuring physical quantities related to body posture changes of the participant through the motion capture system; wherein:

the force measuring system adopts a pressure mat, and the measured physical quantities related to the used forces of the participant comprise a pressure of the participant on the pressure mat and a gravity center position on the pressure mat; and the motion capture system adopts at least two inertial sensors, and the measured physical quantities related to the body posture changes of the participant comprise an angular velocity and a linear acceleration; alternatively, the motion capture system adopts at least one photographing device and more than one visual identification tag, and the measured physical quantities related to the body posture changes of the participant comprise a movement speed and a rotational angular velocity;

(S2), through the signal collecting system, collecting the measured physical quantities and processing with time synchronization;

(S3), through a calculating unit of the information processing system, calculating data after time synchronization, and obtaining multiple characteristic parameters which represent muscle characteristics and/or joint characteristics;

(S4), through a classifying unit of the information processing system, according to categories of the muscle characteristics and/or the joint characteristics, classifying the characteristic parameters into parameter sets of the corresponding categories;

(S5), through a score-generating unit of the information processing system, individually scoring the different characteristic parameters in each parameter set, obtaining an individual score of each characteristic parameter, then weighting according to a relevancy to the corresponding category of the muscle characteristic and/or the joint characteristic, and obtaining a parameter composite score of a specified muscle group and/or joint corresponding to the fitness movement;

(S6), comparing the parameter composite score of each parameter set with a standard parameter score, so as to grade the parameter composite score and obtain a level of each muscle characteristic and/or joint characteristic corresponding to the fitness movement, wherein the standard parameter score is a set standard physical parameter value or a mean value of statistical data of a same age group; and (S7), according to the parameter composite score or a level of each specified muscle group corresponding to the fitness movement, generating a series of muscle characteristic diagrams, wherein a position of each specified muscle group is marked in the muscle characteristic diagram and the muscle characteristics are reflected through different colors; according to the parameter composite score or a level of each specified joint corresponding to the fitness movement, generating a series of joint characteristic diagrams, wherein a position of each specified joint is marked in the joint characteristic diagram and the joint characteristics are reflected through different colors.

2. The human physical functional ability and muscle ability comprehensive assessment method, as recited in claim 1, wherein: in the step (S5), the step of "individually scoring the different characteristic parameters in each parameter set" particularly comprises steps of: dividing a large amount of the statistical characteristic parameters into multiple regions from large to small, wherein each region corresponds to one score, so that a standard score planning table is formed; comparing each measured characteristic parameter with the standard score planning table; and obtaining a corresponding individual score.

3. The human physical functional ability and muscle ability comprehensive assessment method, as recited in claim 1, wherein: the fitness movement refers to at least one kind of push-up, vertical jumping, crunch, trunk forward bending, speed walking, one-leg standing and high-knee lift;

the muscle characteristics comprise a muscle endurance, a muscle explosiveness and a muscle strength; and the muscle strength comprises an upper body strength, a lower body strength and a core strength;

through the movement of vertical jumping, characteristic parameters representing the muscle explosiveness and the lower body strength are able to be measured, comprising a thrust force, an explosiveness and a muscle balance degree of two legs;

through the movement of push-up, characteristic parameters representing the upper body strength are able to be measured, comprising a total thrust force, an average thrust force, a maximum thrust force, fatigue points and a complete number;

through the movement of crunch, characteristic parameters representing the core strength are able to be measured, comprising the complete number, the fatigue points and an average bending angle;

through the movement of high-knee lift, characteristic parameters representing the muscle endurance are able to be measured, comprising the complete number, a highest frequency, a time of reaching the highest frequency and a duration time at the highest frequency.

4. The human physical functional ability and muscle ability comprehensive assessment method, as recited in claim 3, wherein: through the multiple kinds of the fitness movements, parameter composite scores of other characteristics representing a physical sports ability are able to be measured; the other characteristics representing the physical sports ability comprise at least one of flexibility, balance degree and agility;

through the movement of trunk forward bending, characteristic parameters representing the flexibility are able to be measured, comprising a forward bending angle and a time of reaching a maximum angle;

through the movement of speed walking, characteristic parameters representing the agility are able to be measured, comprising the complete number, the highest frequency, the time of reaching the highest frequency and the duration time at the highest frequency; and through the movement of one-leg standing, characteristic parameters representing the balance degree are able to be measured, comprising a balance score, an average gravity center shift, a gravity center shift variance and a balance maintaining ratio.

\* \* \* \* \*